US008685083B2

(12) United States Patent
Perier et al.

(10) Patent No.: US 8,685,083 B2
(45) Date of Patent: Apr. 1, 2014

(54) APPARATUS, SYSTEM, AND METHOD FOR TREATMENT OF POSTERIOR LEAFLET PROLAPSE

(75) Inventors: Patrick Perier, Paris (FR); Vaso Adzich, Santa Ana, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 1821 days.

(21) Appl. No.: 11/474,740

(22) Filed: Jun. 26, 2006

(65) Prior Publication Data
US 2007/0123979 A1   May 31, 2007

Related U.S. Application Data

(60) Provisional application No. 60/694,479, filed on Jun. 27, 2005.

(51) Int. Cl.
*A61F 2/24* (2006.01)
(52) U.S. Cl.
USPC ......................................... 623/2.11; 623/2.26
(58) Field of Classification Search
USPC .................................. 623/2.1, 2.36, 2.37, 2.41
See application file for complete search history.

(56) References Cited

U.S. PATENT DOCUMENTS

| | | | |
|---|---|---|---|
| 3,656,185 A | 4/1972 | Carpentier | |
| 4,055,861 A | 11/1977 | Carpentier et al. | |
| 4,164,046 A | 8/1979 | Cooley | |
| 4,217,665 A | 8/1980 | Bex et al. | |
| 4,275,469 A | 6/1981 | Gabbay | |
| 4,602,911 A | 7/1986 | Ahmadi et al. | |
| 4,790,844 A | 12/1988 | Ovil | |
| 4,917,097 A | 4/1990 | Proudian et al. | |

(Continued)

FOREIGN PATENT DOCUMENTS

| | | |
|---|---|---|
| EP | 0 338 994 | 10/1989 |
| EP | 0 595 791 | 5/1994 |

(Continued)

OTHER PUBLICATIONS

Adams, David, et al., "Large Annuloplasty Rings Facilitate Mitral Valve Repair in Barlow's Disease," Society of Thoracic Surgeons 42$^{nd}$ Annual Meeting, Jan. 30-Feb. 1, 2006.

(Continued)

*Primary Examiner* — David Isabella
*Assistant Examiner* — Joshua Levine
(74) *Attorney, Agent, or Firm* — AnneMarrie Kaiser; Richard B. Cates

(57) ABSTRACT

The invention is an apparatus, system, and method for repairing heart valves. A suture line is secured to a papillary muscle, and then passed through a portion of a heart valve leaflet. A reference element is provided at a desired distance from a plane defined by the heart valve annulus. The suture line is secured to the heart valve leaflet at a position adjacent the reference element. The reference element may part of a device configured for placement on or in a heart valve annulus. The reference element may be slidingly secured to the device so that the distance of the reference element from the main body of the device can be varied by a surgeon or other user. The reference element may be a line of suture, which may be pre-installed during manufacture of the device or may be installed by the surgeon or other user.

11 Claims, 17 Drawing Sheets

(56) References Cited

U.S. PATENT DOCUMENTS

| | | |
|---|---|---|
| 4,993,428 A | 2/1991 | Arms |
| 5,010,892 A | 4/1991 | Colvin et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,316,016 A | 5/1994 | Adams et al. |
| 5,344,442 A | 9/1994 | Deac |
| 5,396,887 A | 3/1995 | Imran |
| 5,450,860 A | 9/1995 | O'Connor |
| 5,480,424 A | 1/1996 | Cox |
| 5,496,336 A | 3/1996 | Cosgrove et al. |
| 5,533,515 A | 7/1996 | Coller et al. |
| 5,573,007 A | 11/1996 | Bobo, Sr. |
| 5,593,435 A | 1/1997 | Carpentier et al. |
| 5,607,471 A | 3/1997 | Seguin et al. |
| 5,662,704 A | 9/1997 | Gross |
| 5,662,705 A | 9/1997 | Love et al. |
| 5,674,279 A | 10/1997 | Wright et al. |
| 5,728,064 A | 3/1998 | Burns et al. |
| 5,733,331 A | 3/1998 | Pereredo |
| 5,752,522 A | 5/1998 | Murphy |
| 5,776,189 A | 7/1998 | Khalid |
| 5,814,098 A | 9/1998 | Hinnenkamp et al. |
| 5,824,066 A | 10/1998 | Gross |
| 5,824,069 A | 10/1998 | Lemole |
| 5,848,969 A | 12/1998 | Panescu et al. |
| 5,855,563 A | 1/1999 | Kaplan et al. |
| 5,865,801 A | 2/1999 | Houser |
| 5,888,240 A | 3/1999 | Carpentier et al. |
| 5,902,308 A | 5/1999 | Murphy |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,931,868 A | 8/1999 | Gross |
| 5,961,440 A | 10/1999 | Schweich, Jr. et al. |
| 5,972,030 A | 10/1999 | Garrison et al. |
| 6,010,531 A | 1/2000 | Donlon et al. |
| 6,019,739 A | 2/2000 | Rhee et al. |
| 6,024,918 A | 2/2000 | Hendriks et al. |
| 6,066,160 A | 5/2000 | Colvin et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,110,200 A | 8/2000 | Hinnenkamp |
| 6,117,091 A | 9/2000 | Young et al. |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,312,464 B1 | 11/2001 | Navia |
| 6,332,893 B1 | 12/2001 | Mortier et al. |
| 6,358,277 B1 * | 3/2002 | Duran .................. 623/2.12 |
| 6,391,054 B2 | 5/2002 | Carpentier et al. |
| 6,406,420 B1 | 6/2002 | McCarthy et al. |
| 6,406,493 B1 | 6/2002 | Tu et al. |
| 6,409,759 B1 | 6/2002 | Peredo |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,723,038 B1 | 4/2004 | Schroeder et al. |
| 6,726,715 B2 | 4/2004 | Sutherland |
| 6,726,717 B2 | 4/2004 | Alfieri et al. |
| 6,749,630 B2 | 6/2004 | McCarthy et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,830,586 B2 | 12/2004 | Quijano et al. |
| 6,858,039 B2 | 2/2005 | McCarthy |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,945,996 B2 | 9/2005 | Sedransk |
| 6,955,689 B2 | 10/2005 | Ryan et al. |
| 6,966,924 B2 | 11/2005 | Holmberg |
| 6,977,950 B1 | 12/2005 | Krishnamoorthy |
| 6,986,775 B2 | 1/2006 | Morales et al. |
| 7,037,334 B1 | 5/2006 | Hlavka et al. |
| 7,066,954 B2 | 6/2006 | Ryan et al. |
| 7,101,395 B2 | 9/2006 | Tremulis et al. |
| 7,112,219 B2 | 9/2006 | Vidlund et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,247,134 B2 | 7/2007 | Vidlund et al. |
| 7,294,148 B2 | 11/2007 | McCarthy |
| 7,329,280 B2 | 2/2008 | Bolling et al. |
| 7,527,647 B2 | 5/2009 | Spence |
| 2001/0034551 A1 | 10/2001 | Cox |
| 2002/0029080 A1 * | 3/2002 | Mortier et al. .................. 623/2.36 |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0078653 A1 | 4/2003 | Vesely et al. |
| 2003/0083742 A1 | 5/2003 | Spence et al. |
| 2003/0093148 A1 | 5/2003 | Bolling et al. |
| 2003/0105519 A1 | 6/2003 | Fasol et al. |
| 2004/0006384 A1 | 1/2004 | McCarthy |
| 2004/0088047 A1 | 5/2004 | Spence et al. |
| 2004/0122513 A1 | 6/2004 | Navia et al. |
| 2004/0186566 A1 | 9/2004 | Hindrichs et al. |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0038508 A1 | 2/2005 | Gabbay |
| 2005/0043791 A1 | 2/2005 | McCarthy et al. |
| 2005/0070999 A1 | 3/2005 | Spence |
| 2005/0075727 A1 | 4/2005 | Wheatley |
| 2005/0107871 A1 | 5/2005 | Realyvasquez et al. |
| 2005/0131533 A1 | 6/2005 | Alfieri et al. |
| 2005/0182487 A1 | 8/2005 | McCarthy et al. |
| 2005/0192666 A1 | 9/2005 | McCarthy |
| 2005/0197696 A1 | 9/2005 | Gomez Duran |
| 2005/0246014 A1 | 11/2005 | McCarthy |
| 2005/0256567 A1 | 11/2005 | Lim et al. |
| 2005/0256568 A1 | 11/2005 | Lim et al. |
| 2005/0256569 A1 | 11/2005 | Lim et al. |
| 2005/0267572 A1 | 12/2005 | Schoon et al. |
| 2005/0278022 A1 | 12/2005 | Lim |
| 2005/0288776 A1 | 12/2005 | Shaoulian et al. |
| 2005/0288777 A1 | 12/2005 | Rhee et al. |
| 2005/0288778 A1 | 12/2005 | Shaoulian et al. |
| 2005/0288780 A1 | 12/2005 | Rhee et al. |
| 2005/0288782 A1 | 12/2005 | Moaddeb et al. |
| 2005/0288783 A1 | 12/2005 | Shaoulian et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025856 A1 | 2/2006 | Ryan et al. |
| 2006/0025858 A1 | 2/2006 | Alameddine |
| 2006/0030885 A1 | 2/2006 | Hyde |
| 2006/0149368 A1 | 7/2006 | Spence |
| 2006/0195183 A1 | 8/2006 | Navia et al. |

(56) References Cited

U.S. PATENT DOCUMENTS

| | | |
|---|---|---|
| 2006/0259135 A1 | 11/2006 | Navia et al. |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0123979 A1 | 5/2007 | Perier et al. |
| 2007/0162111 A1 | 7/2007 | Fukamachi et al. |
| 2007/0173930 A1 | 7/2007 | Sogard et al. |
| 2007/0213582 A1 | 9/2007 | Zollinger et al. |
| 2007/0255396 A1 | 11/2007 | Douk et al. |
| 2009/0177278 A1 | 7/2009 | Spence |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |

FOREIGN PATENT DOCUMENTS

| | | |
|---|---|---|
| EP | 0 860 151 | 8/1998 |
| EP | 1 034 753 | 9/2000 |
| FR | 2 708 458 | 8/1993 |
| WO | 91/19465 | 12/1991 |
| WO | WO 91/19456 | 12/1991 |
| WO | WO 95/03757 | 2/1995 |
| WO | WO 96/40008 | 12/1996 |
| WO | WO 97/41801 | 11/1997 |
| WO | WO 97/42871 | 11/1997 |
| WO | WO 98/06329 | 2/1998 |
| WO | WO 99/11201 | 3/1999 |
| WO | WO 99/51169 | 10/1999 |
| WO | WO 99/65423 | 12/1999 |
| WO | WO 00/32105 | 6/2000 |
| WO | WO 01/19292 | 3/2001 |
| WO | WO 01/26586 | 4/2001 |
| WO | WO 01/47438 | 7/2001 |
| WO | WO 01/87191 | 11/2001 |
| WO | WO 02/03892 | 1/2002 |
| WO | WO 03/020178 | 3/2003 |
| WO | WO 03/041617 | 5/2003 |
| WO | WO 2004/004607 | 1/2004 |
| WO | WO 2005/004753 | 1/2005 |
| WO | WO 2005/034813 | 4/2005 |
| WO | WO 2005/082278 | 9/2005 |
| WO | WO 2005/110290 | 11/2005 |
| WO | WO 2006/041877 | 4/2006 |
| WO | WO 2006/133186 | 12/2006 |
| WO | WO 2007/050506 | 5/2007 |
| WO | WO 2007/100408 | 9/2007 |
| WO | WO 2007/131513 | 11/2007 |
| WO | WO 2008/058940 | 5/2008 |
| WO | WO 2008/063537 | 5/2008 |
| WO | WO 2008/094469 | 8/2008 |
| WO | WO 2008/098226 | 8/2008 |

OTHER PUBLICATIONS

Alonso-Lei, M.D., et al., Adjustable Annuloplasty for Tricuspid Insufficiency, the annals of Thoracic Surgery, vol. 46, No. 3, pp. 368-369, Sep. 1988.

Bolling, Mitral Valve Reconstruction in the Patient With Heart Failure, Heart Failure Reviews, 6, pp. 177-185, 2001.

Bolling, et al., Surgical Alternatives for Heart Failure, the Journal of Heart and Lung Transplantation, vol. 20, No. 7, pp. 729-733, 2001.

Carpentier, et al. "The 'Physio-Ring': An Advanced Concept in Mitral Valve Annuloplasty," Society of Thoracic Surgeons $31^{st}$ Annual meeting, Jan. 30-Feb. 2, 1995.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier—Edwards Pyshio Annuloplasty Ring, Edwards Lifesciences Corporation, 2003.

Cochran, et al., Effect of Papillary Muscle Position on Mitral Valve Function: Relationship to Homografts, the Society of Thoracic Surgeons, pp. 5155-5161, 1998.

D.C. Miller, IMR Redux—to Repair or Replace?, Journal of Thoracic & Cardiovascular Surgery, pp. 1-8, 2001.

Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

Melo, et al., Atrioventricular Valve Repair Using Externally Adjustable Flexible Rings: the Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Salgo, et al., Effect of Annular Shape on Leaflet Curvature in Reducing Mitral Leaflet, American Heart Association, Circulation 200; pp. 106-711.

Seguin, et al., Advance in Mitral Valve Repair Using a Device Flexible in Three Dimensions, the St. Jude Medical-Seguin Annuloplasty Ring, ASAIO Journal, vol. 42, No. 6, pp. 368-371, 1996.

Smolens, et al., Mitral Valve Repair in Heart Failure, the European Journal of Heart Failure 2, pp. 365-371, 2000.

Techniques for 3D Quantitative Echocardiography, University of Washington Cardiovascular Research & Training Center Cardiac Imaging Research Lab, pp. 1-5, Oct. 2003.

Watanabe, Nozomi, et al. "Mitral Annulus Flattens in Ischemic Mitral Regurgitation: Geometric Differences Between Inferior and Anterior Myocardial Infarction: a Real-Time 3-Dimensional Echocardiographic Study," American Heart Association © 2005; ISSN: 1524-4539.

* cited by examiner

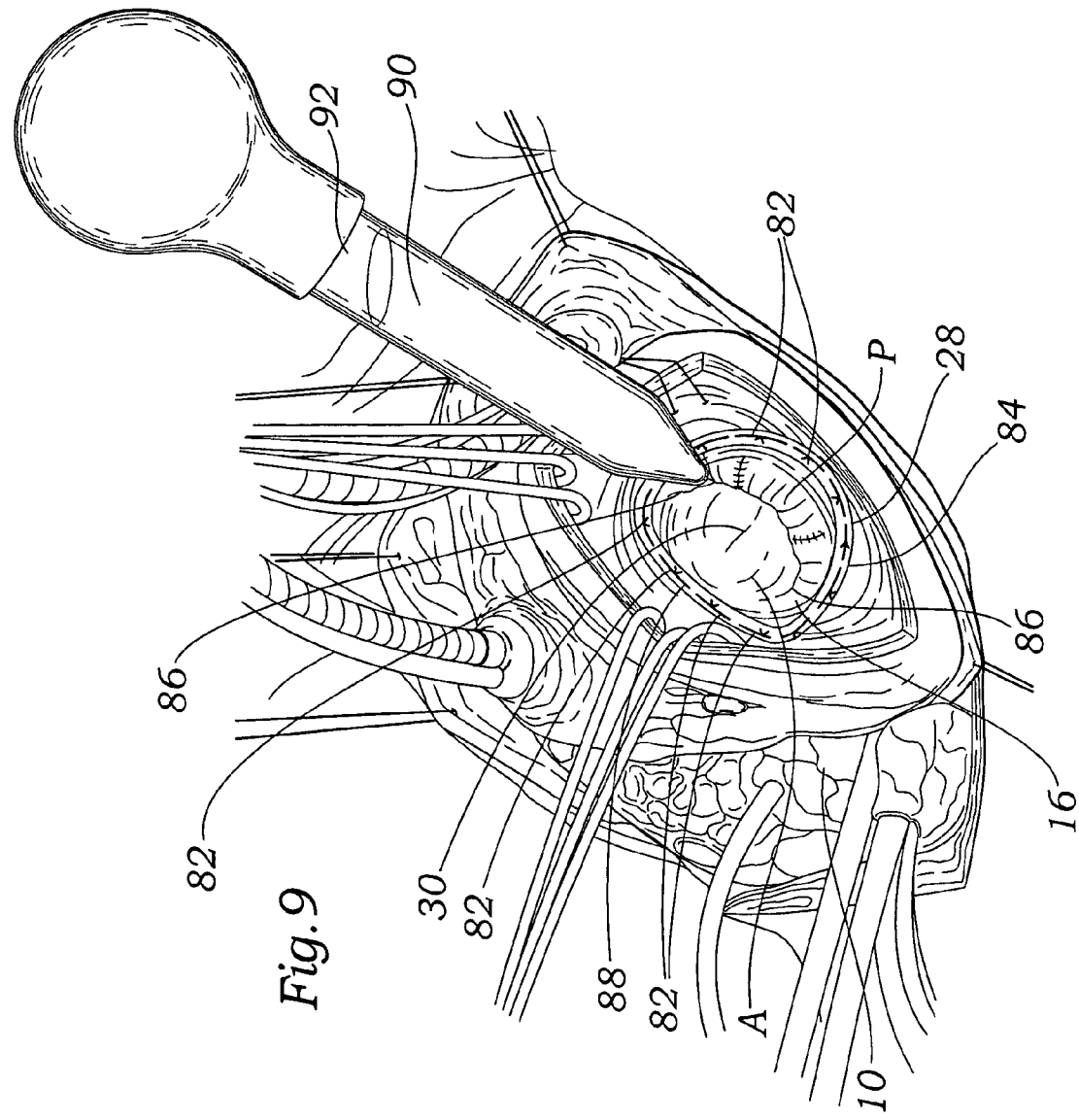

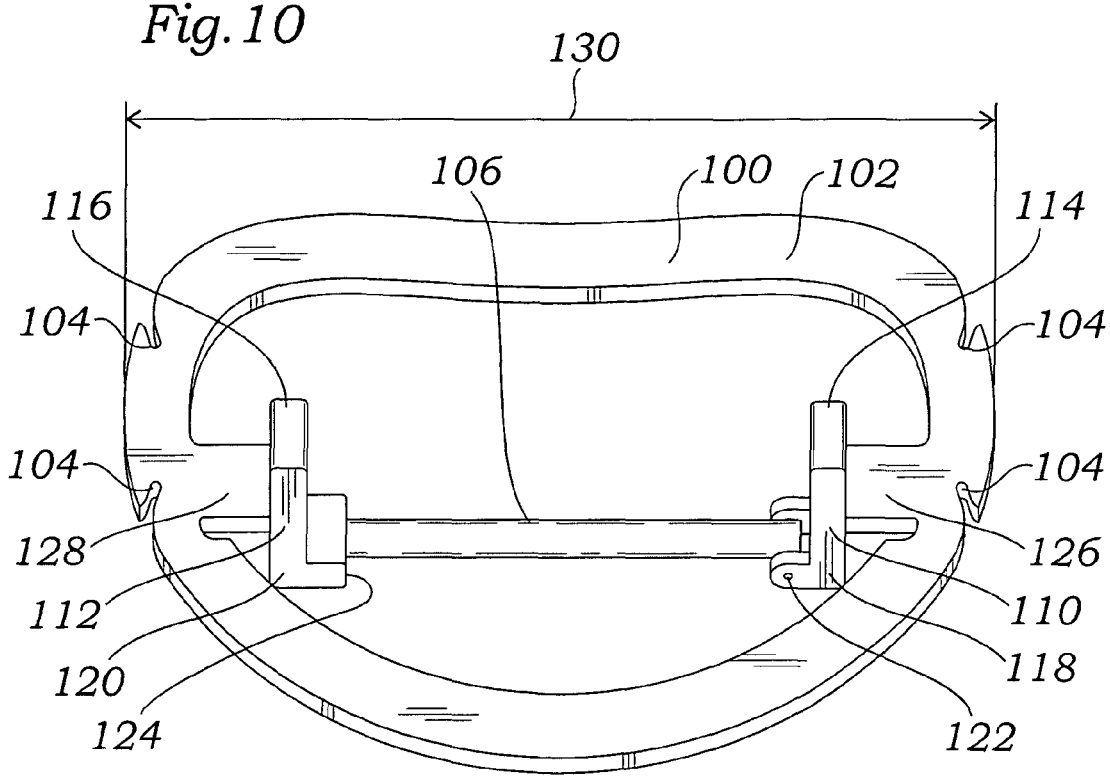
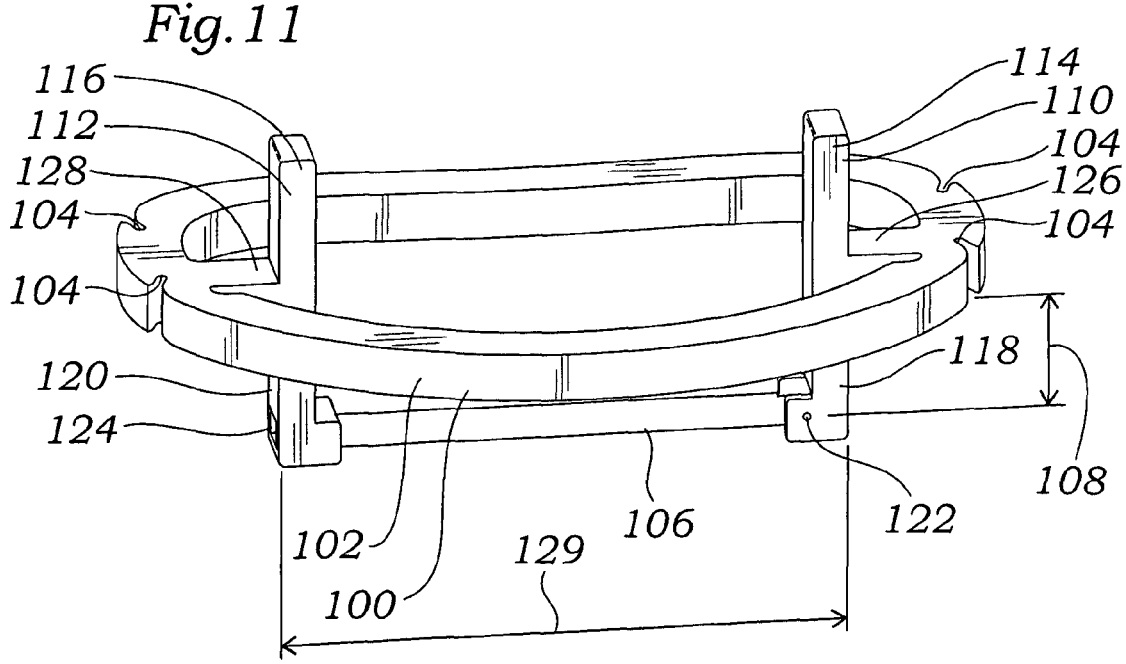

APPARATUS, SYSTEM, AND METHOD FOR TREATMENT OF POSTERIOR LEAFLET PROLAPSE

CROSS-REFERENCES TO RELATED APPLICATIONS

This application claims priority to commonly assigned U.S. provisional patent application No. 60/694,479 filed Jun. 27, 2005, which is incorporated herein by reference in its entirety for all purposes.

FIELD OF THE INVENTION

The present invention relates generally to medical devices and particularly to repairing posterior leaflet prolapse in a mitral valve.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid, and pulmonary, and are each mounted in an annulus comprising dense fibrous rings. The mitral and tricuspid valves have thread-like bands of fibrous tissue that attach to the valve at one end and to the papillary muscles at the other end.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated.

Various surgical techniques may be used to repair a diseased or damaged valve. One method for treating defective valves is through repair or reconstruction. One repair technique that has been shown to be effective in treating incompetence is annuloplasty, in which the effective size and/or shape of the valve annulus is modified by securing a repair segment, such as an annuloplasty ring, around the heart valve annulus. For example, the valve annulus may be contracted by attaching a prosthetic annuloplasty repair segment or ring to an interior wall of the heart around the valve annulus. The annuloplasty ring is designed to support the functional changes that occur during the cardiac cycle: maintaining coaptation and valve integrity to prevent reverse flow while permitting good hemodynamics during forward flow.

The annuloplasty ring typically comprises an inner substrate, often formed from a metal (such as stainless steel or titanium) or from a flexible material (such as silicone rubber or Dacron cordage), which is typically covered with a biocompatible fabric or cloth to allow the ring to be sutured to the heart tissue. Depending on a particular application, annuloplasty rings may be stiff or flexible, may be split or continuous, and may have a variety of shapes, including circular, D-shaped, C-shaped, saddle-shaped, and/or kidney-shaped. Examples are seen in U.S. Pat. Nos. 5,041,130, 5,104,407, 5,201,880, 5,258,021, 5,607,471, 6,187,040, and 6,805,710, the contents of which are incorporated herein by reference in their entirety. Many annuloplasty rings are formed in a plane, but some rings are generally non-planar. Such non-planar rings can be saddle-shaped, and/or bowed along various portions, such as being bowed along their anterior or straight side to conform to the desired shape of the annulus at that location.

In many diseased valves, the chordae tendineae are either ruptured, otherwise damaged, or of an improper length. When chordae tendineae are too long, too short, or otherwise damaged, the corresponding tricuspid or mitral valve to which they are attached typically may fail to close properly. For example, chordae tendineae which are ruptured or are too long allow a valve to prolapse, wherein one or more valve leaflets swing backward past their proper closed position. This can lead to regurgitation, which is the unwanted backflow of blood from a ventricle to an atrium resulting from imperfections in the valve. When the valve allows such backward flow into an atrium, the corresponding ventricle must pump progressively harder to circulate blood throughout the body, which in turn promotes congestive heart failure.

Repairing and/or replacing dysfunctional chordae tendineae has been performed for some time. The techniques for such repair are often complicated due to the difficulties in accessing the surgical site, in identifying the dysfunctional chordae tendineae, and in determining the proper length for the repaired and/or replacement chordae tendineae.

Another approach to valve repair involves surgical excision of all or a portion of one or more of the valve leaflets of the particular heart valve. In such a procedure, a damaged portion of a valve leaflet is excised, with the remaining portions of the valve leaflet stitched together to repair the opening created by the removal of the damaged portion. This procedure tightens the valve leaflet, which can prevent valve prolapse and thereby improve valve function. An example of such a procedure is a segmental resection of the mitral valve, wherein a prolapsing portion of a posterior leaflet is excised and the remaining portions sewed together to tighten the leaflet.

Quadrangular resection of the prolapsed area is a relatively common valve repair technique which has demonstrated excellent results. However, the technique is relatively complex and can require the surgeon to make numerous real-time decisions during the course of the procedure, including determining how large to make the resection, whether to perform an annulus plication to close the gap, etc.

The goal of mitral valve repair is to restore a good surface of coaptation to ensure satisfactory function of the valve. Because leaflet tissue is the primary component defining the surface of coaptation of the valve, it may be preferable to preserve as much as possible of the leaflet tissue, as opposed to resecting significant portions thereof. Preserving as much tissue as possible maintains anatomic and dynamic relationships, allowing for better distribution of forces and stresses on the valve components. However, in order to preserve the leaflet tissue, other aspects of the dysfunctional valve may have to be modified and/or treated, such as the shape of the valve annulus and any damaged chordae.

Accordingly, there has been a need for an improved apparatus, system, and method to repair dysfunctional heart valves, including mitral valves. The present invention satisfies one or more of these needs.

SUMMARY OF THE INVENTION

The present application is generally described with respect to its use in the repair of the mitral valve, which regulates blood flow from the left atrium (LA) to the left ventricle (LV). However, the invention could also be applied to repair of other valves, such as the tricuspid or aortic valve repairs.

The invention includes correction of mitral valve prolapse using replacement chordae, such as expanded neochordae suture (such as ployetetrafluroethylene (e-PTFE)) without leaflet resection, or with minimal leaflet resection, to resuspend the free edge of the posterior leaflet. One or more replacement chordae sutures can be passed through the papillary muscle and through the leaflet, adjusted to the proper length, and tied in position. The desired number and length of the replacement chordae depends on the needs of the particular patient, including characteristics of the valve annulus, the valve leaflets, and the existing chordae.

The invention can include application of a heart valve annuloplasty ring. The annuloplasty ring can reshape the heart valve annulus to a desired shape, and/or prevent the heart valve annulus from further and undesired deformation. The annuloplasty ring can also fix the valve annulus in the systolic position.

The invention can also include modifications to the valve leaflet itself. For example, the surgeon may suture the indentations on the valve leaflet, particularly where the indentations are relatively deep and where an annuloplasty ring is used to fix the valve annulus in the systolic position.

Various aspects of the invention can be used individually or in combination to repair a valve. The invention is applicable to various ways of accessing the valve for repair, including an open surgical approach such as sternotomy, or a minimally-invasive approach such as percutaneous or intercostal. The standard atriotomy approach is often used for mitral valve repair procedures.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIG. 9 is top view of a mitral valve with an annuloplasty ring implanted and with a saline injector;

FIG. 10 is a top perspective view of a guide device according to an embodiment of the invention;

FIG. 11 is a side perspective view of the guide device of FIG. 10;

DETAILED DESCRIPTION OF THE INVENTION

Figure 1:
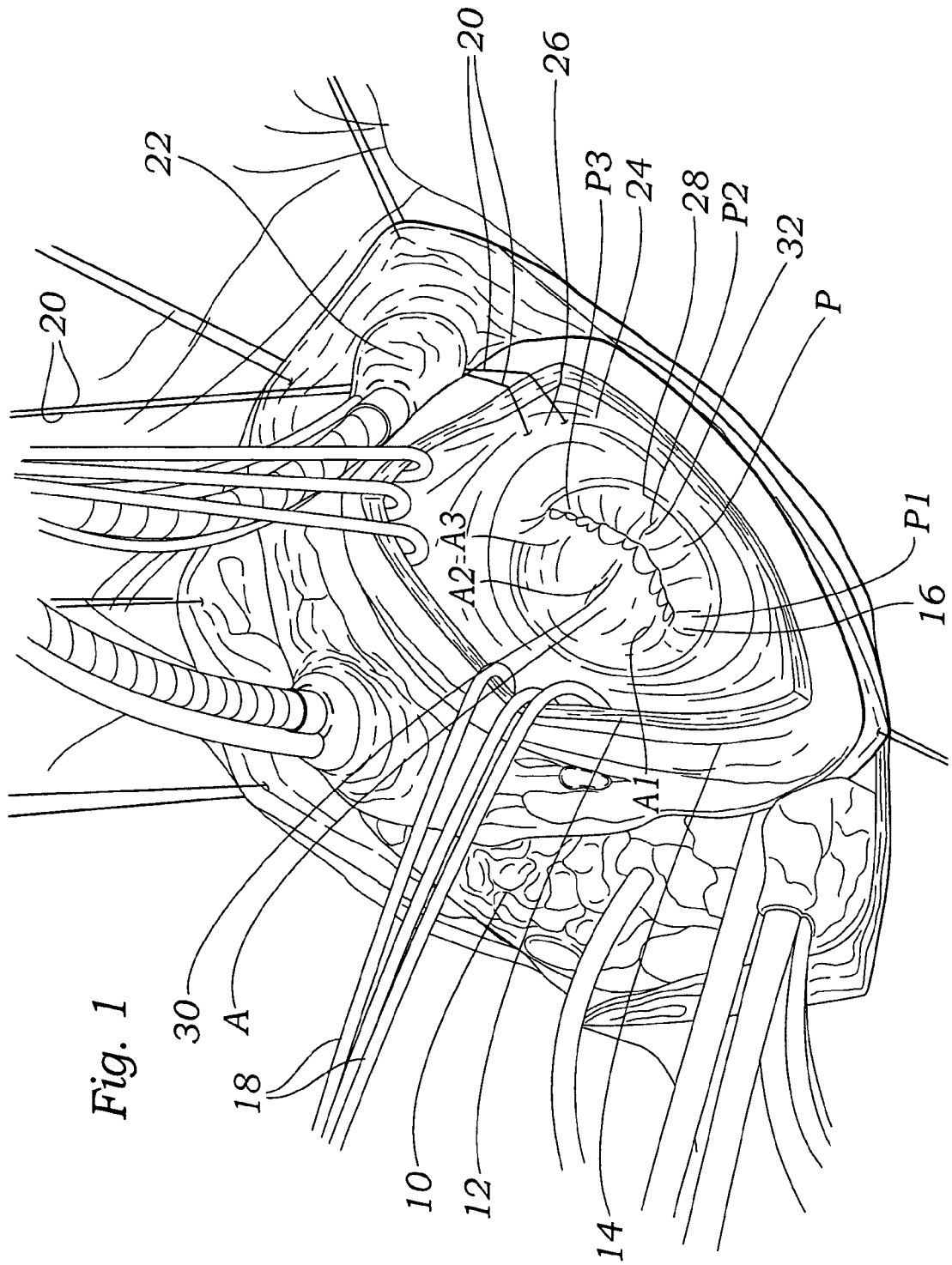
FIG. 1 depicts a top view of a mitral valve being exposed for viewing and analysis by the surgeon.

FIG. 1 depicts a heart 10 with an incision 12 in the left atrial wall 14 through which the mitral valve 16 is exposed for viewing during a surgical proceeding. The atrial wall incision 12 is held open with one or more retractors 18, giving the surgeon a full view for analysis of the mitral valve 16. Note that the viewing can be achieved directly a shown, as is typically the case for open chest and/or open heart surgical methods, or indirectly through an endoscope or other visualization devices, as may be used for minimally invasive procedures. In the exposure depicted in FIG. 1, a suture 20 (such as a 3-0 suture) is passed around and below the inferior vena cava 22, then makes a shallow pass through (i.e., takes a superficial bite of) the left atrial endothelium 24 at a position 26 about 1.5 cm behind the mitral valve annulus 28. Note that in the particular embodiment depicted, the suture is passed through the left atrial endothelium 18 at approximately the 5 o'clock position on the valve annulus 28, with noon being the middle 22 of the anterior leaflet A and 6 o-clock being the middle 24 of the posterior leaflet P), and then passes back behind and below the inferior vena cava 16. By applying a gentle tug on the suture 20, the desired exposure can be achieved.

Once the desired exposure and/or viewing of the mitral valve 16 are achieved, a thorough surgical analysis of the mitral valve structure can be performed. An alphanumeric code is often used to designate areas of the mitral valve 16, and this code is used in this application and its drawings. The letters P and A refer to the posterior leaflet P and anterior leaflet A, respectively. Each leaflet is also divided into three portions, with the antero-lateral portion of the leaflet designated with the number 1, the middle portion with the number 2, and the postero-medial portion with the number 3. The posterior leaflet portions are typically referred to as scallops due to their shapes, with the antero-lateral scallop designated as P1, the middle scallop designated as P2, and the postero-medial scallop designated as P3. Corresponding (i.e., opposing) portions of the anterior leaflet are designated as A1, A2, and A3, respectively.

Figure 2:
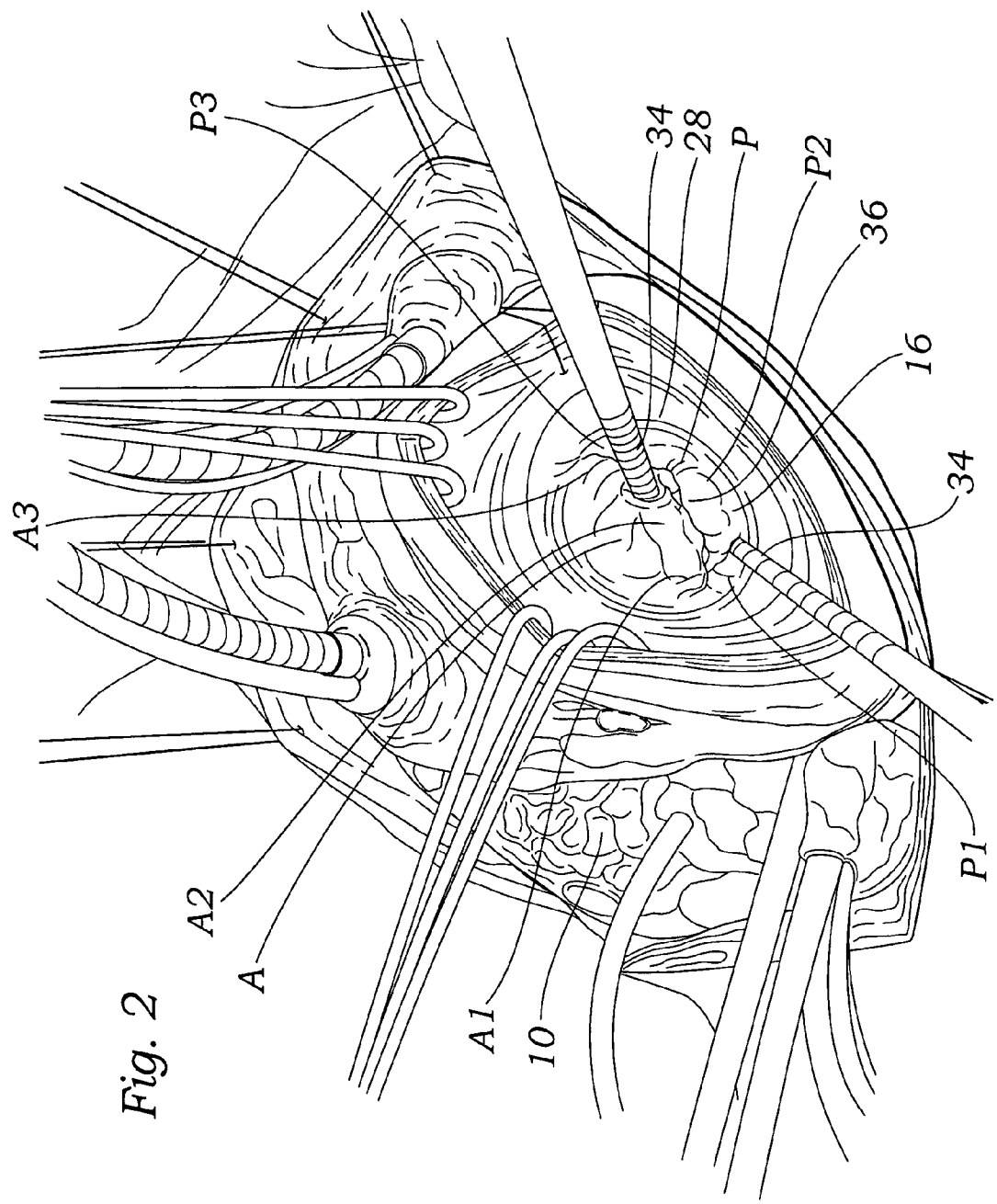
FIG. 2 depicts a top view of a mitral valve being analyzed by a surgeon.

Usually the antero-lateral scallop P1 of the posterior leaflet P is free from prolapse and can be used as a reference point with which to compare the other segments. With the help of one or more nerve hooks 34 or similar devices, as depicted in FIG. 2, the free edge of P1 is compared to free edges or other portions of A1, then to A2, P2, A3, and P3. Note that this order of comparison is just one example, and the invention is not limited to this specific order. Using such a step-by-step exploration of essentially the entire mitral valve, it is possible to achieve a good three-dimensional understanding of the mitral valve. This analysis can determine and/or identify prolapse or other dysfunction in the valve. In the particular mitral valve 16 depicted in FIG. 2, the analysis reveals a prolapse 36 of the posterior leaflet P, located in P2 in which the free edge of the posterior leaflet middle scallop P2 overrides the free edge of the anterior leaflet middle portion A2 due to one or more ruptured chordae 38 (shown in FIG. 3). Note that the result of the surgical valve analysis can be compared to the intraoperative echo findings.

Figure 3:
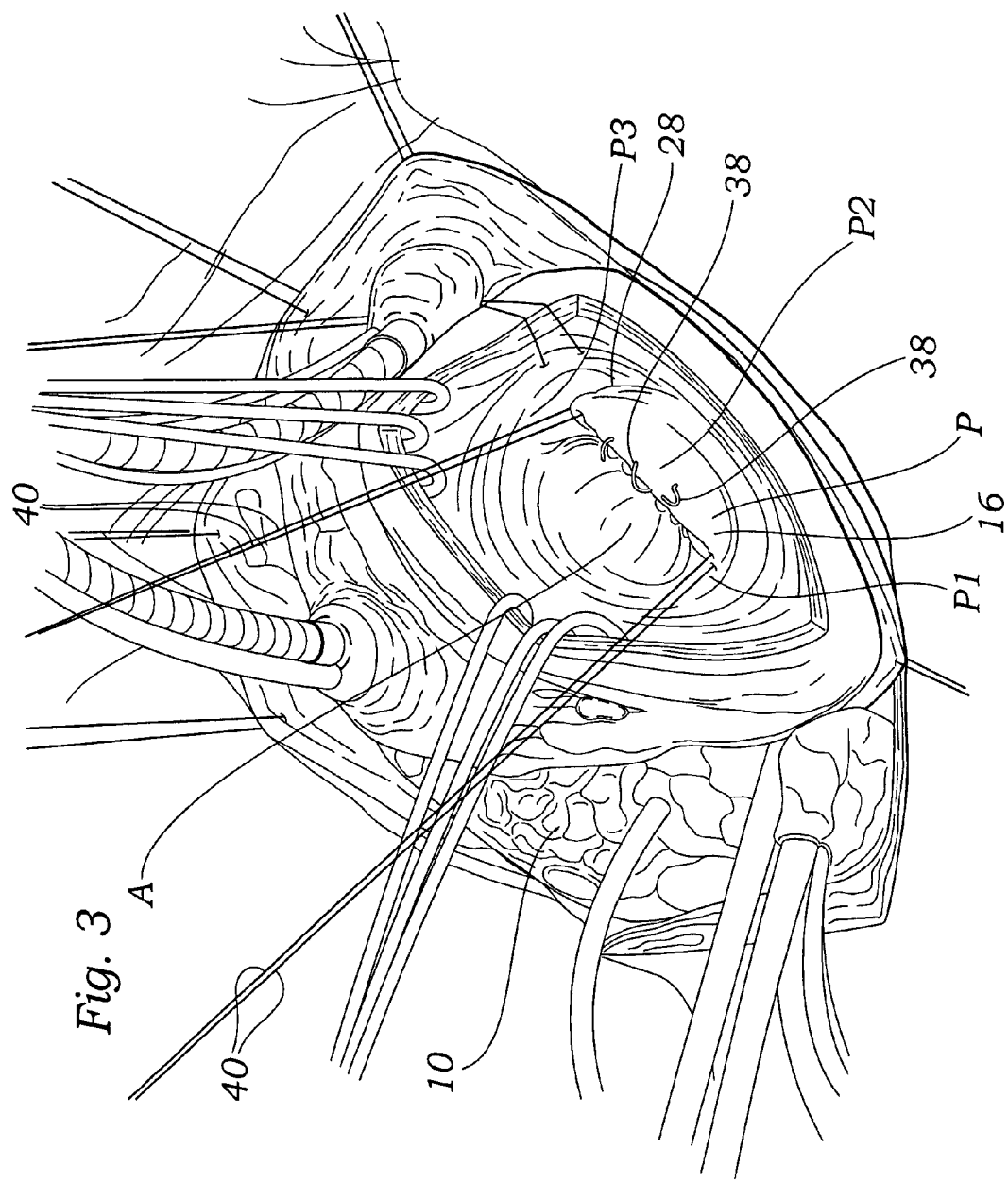
FIG. 3 depicts a top view of a mitral valve under analysis of the prolapsed area of the mitral valve posterior leaflet.

Once the prolapsed area (or areas) of the posterior leaflet P is identified, one or more stay sutures 40 (such as 2-0 stay sutures) are be passed around the normal chordae, and/or through the posterior leaflet P itself (as depicted in FIG. 3), on each side of the prolapsed area 36 of the posterior leaflet P to delineate the pathological zone. Gentle pressure on these stay sutures 40 will provide exposure of the prolapsed area 36 and ruptured chordae 38, as depicted in FIG. 3.

Analysis of the prolapsed area 36 is directed toward two main aspects of the tissue: the quality of the tissue, and the quantity/amount of tissue (which corresponds to the height of the posterior leaflet P in the prolapsed area). In considering the quality of the tissue, the presence and extent of mucoid degeneration should be assessed. The aim of the operation is to construct a vertical buttress in which the surface area is generally smooth and flat to ensure an even surface for coaptation. Mucoid degeneration may be too irregular, producing bulging pockets which make the surface of coaptation uneven and irregular. In such a case, a resection to remove such uneven areas may be necessary. Mucoid degeneration may also be too excessive at the base of the posterior leaflet P, reducing the pliability of the junction between the mitral valve annulus 28 and posterior leaflet P. This can displace the surface of coaptation anteriorly, which may increase the risk of systolic anterior motion (SAM). SAM occurs when the anterior leaflet of the mitral valve is "pulled" into the outflow of the left ventricle during the systolic phase, which can cause leakage through the mitral valve into the left atrium.

In assessing the quantity of tissue, the surgeon will evaluate the height of the posterior leaflet P. An excess of tissue is considered to be present when the height of the posterior leaflet P exceeds 2 cm. It is important to take note of such a situation, because it will affect the length of the artificial chordae to be implanted.

Figure 4:
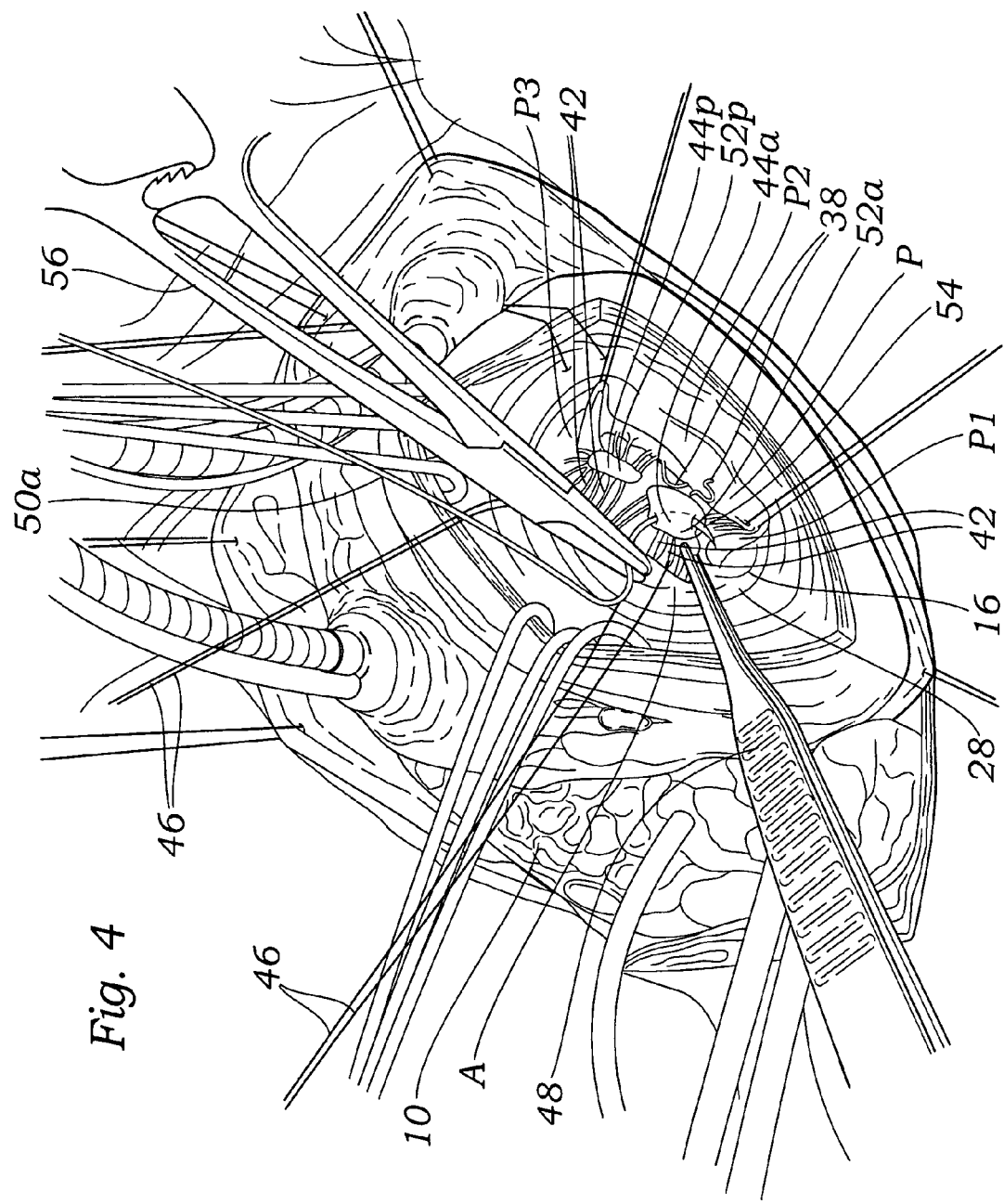
FIG. 4. depicts a top view through a mitral valve with placement of artificial chordae suture through the papillary muscle.

To provide a better view of and/or access to the area of the chordae 42 and the papillary muscles 44a, 44p, one or more anterior stay sutures 46, such as 2-0 stay sutures, are passed around the chordae 42 of the anterior leaflet A, as depicted in FIG. 4. Two such sutures 46 may be sufficient, depending on the particular application and patient. Gentle pulling on these anterior stay sutures 46, when combined with gentle pulling on the posterior stay sutures 40 and hence on the posterior leaflet P, provides good views and/or access into the left ventricular cavity and to the papillary muscles 44a, 44p. Using a forceps 48, it is then relatively convenient to grasp the anterior papillary muscle 44a to improve its exposure and stability. A chordae replacement suture 50a, such as mattress suture of 4-0 e-PTFE, is placed through the fibrotic part of the top 52a of the anterior papillary muscle 44a. In the embodiment depicted, the chordae replacement suture 50a is placed using a curved needle 54 and needle holder 56. It is often desirable that the exit point of the suture 50a be oriented towards the prolapsed area 36. The chordae replacement suture 50a is then tied down, which can involve three or four knots, on the anterior papillary muscle 44a. The same maneuver may then be repeated for the posterior papillary muscle 44p, whereby chordae replacement suture 50p (depicted in FIG. 5A) is passed through the fibrotic part of the top 52p of the posterior papillary muscle 44p.

To respect and protect the structure of the subvalvular apparatus (e.g., chordae, etc.), it is often desirable that the chordae replacement sutures 50a, 50p be placed through the papillary muscle head(s) that anchors the diseased chordae being replaced and/or repaired. The actual placement of the chordae replacement sutures 50a, 50p depends on the particular application, including the particular patient and surgeon. The main principle is that the artificial chordae are securely anchored.

Prolapses are most typically localized, such as the localized prolapse 36 of the middle scallop P2 of the posterior leaflet P depicted. However, extensive lesions or other elements, which may include abnormalities in other portions of the leaflet(s), may complicate the repair. For example, if the prolapsed area 36 of the posterior leaflet P is greater than just the middle portion of middle scallop P2, or if other lesions and/or aspects are present, installation of additional artificial chordae may be needed to resuspend the prolapsed area 36.

Figure 5A:
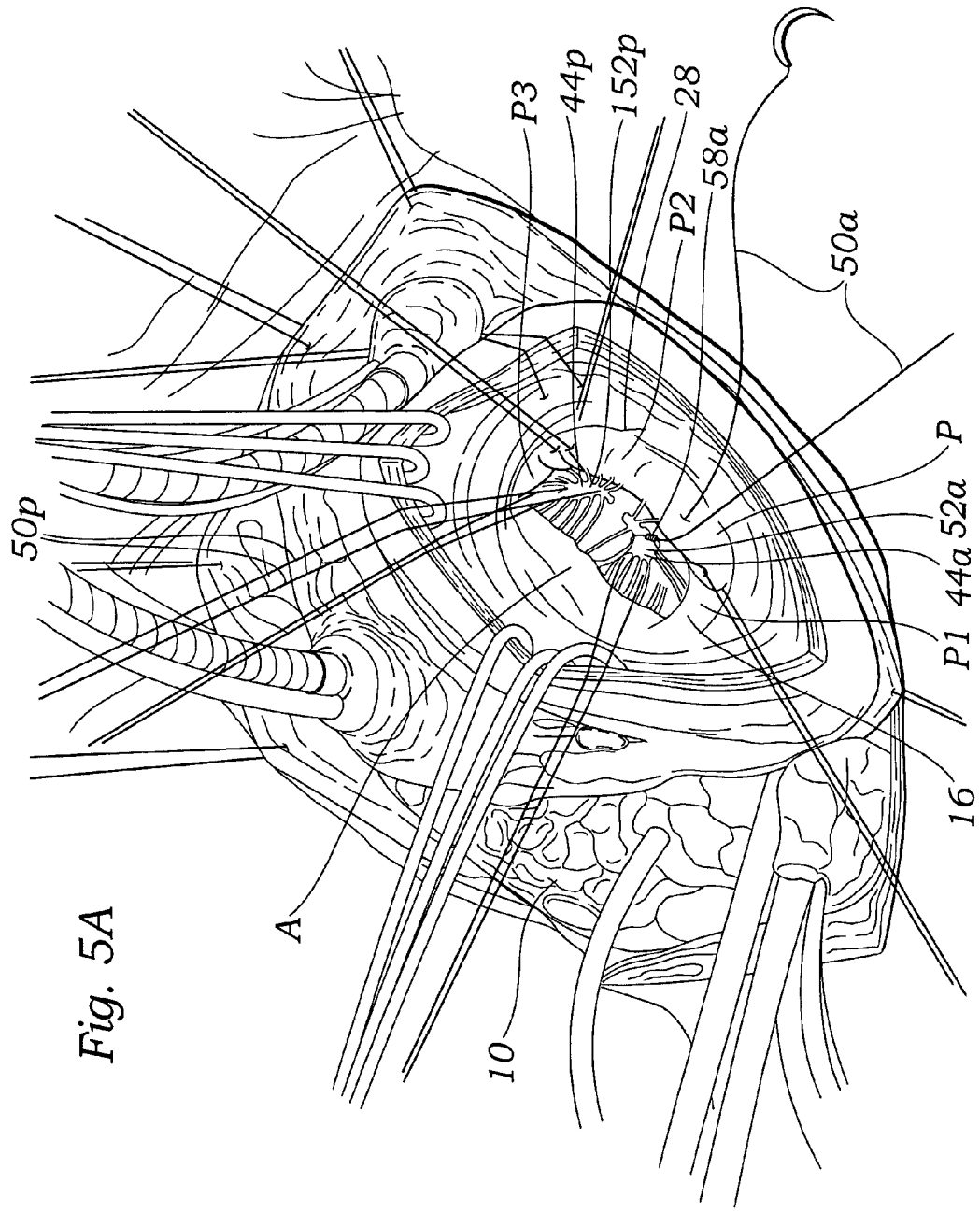
FIG. 5A depicts a top view of a mitral valve with placement of artificial chordae suture through the free edge of the posterior leaflet.
Figure 5B:
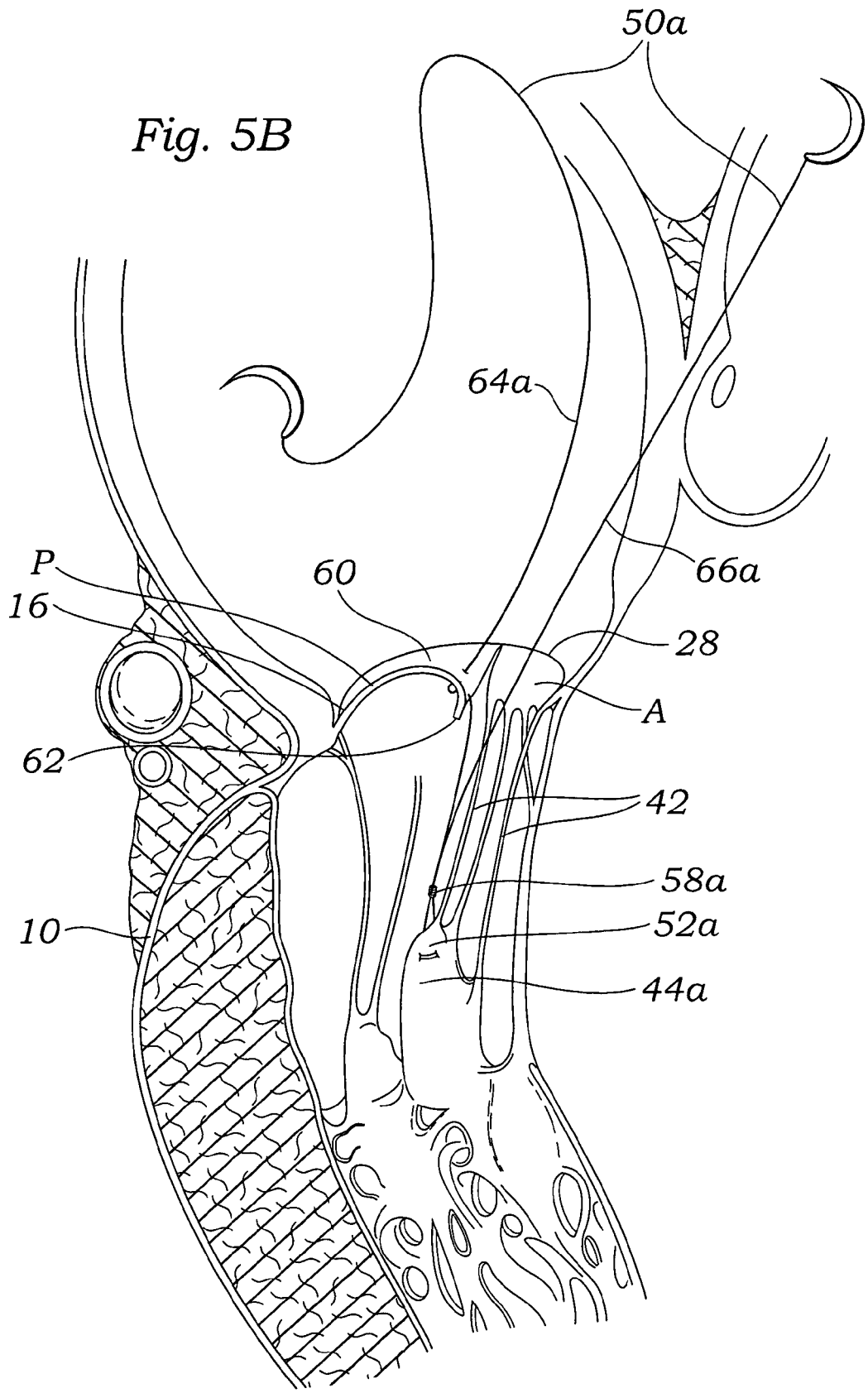
FIG. 5B depicts a side view of a mitral valve with placement of artificial chordae suture through the free edge of the posterior leaflet.

With the chordae replacement sutures 50a, 50p passed through and tied via knots 58a (58p not shown) to the desired papillary muscle or muscles 44a, 44p, the chordae replacement sutures 50a, 50p are then brought up through the free margin(s) of the leaflet, which in the embodiment depicted is the posterior leaflet P. In bringing the chordae replacement sutures 50a, 50p up, care is taken to avoid entangling the chordae replacement sutures 50a, 50p in the native non-diseased chordae 42 or other subvalvular elements. In the embodiment of FIGS. 5A and 5B, one suture 50a is placed between the middle of P2 and the indentation between P1-P2. (The other suture 50p will be placed between the middle of P2 and the indentation P2-P3, although this procedure is not depicted in FIGS. 5A and 5B.)

In the embodiment depicted more clearly in FIG. 5B, the double-armed suture 50a is passed through the auricular side 60 of the posterior leaflet P at and/or adjacent the free edge 62 where the natural chordae were/are attached, and then back through to the auricular side 60 about 4 to 5 mm away from the free edge 62. The distance between the two arms 64, 66 of suture 50a as they pass through the posterior leaflet P may be approximately 3 mm to avoid plication and/or damage of the leaflet tissue which might impair the smoothness and regularity of the surface of coaptation.

Note that the procedure depicted in FIGS. 5A and 5B only shows the tying and connection of chordae replacement suture 50a to the posterior leaflet P and anterior papillary muscle 44a. Where desired, and depending on the particular application, the procedure may be repeated to connect chordae replacement suture 50p (where present) to the posterior leaflet P and posterior papillary muscle 44p, or to any leaflet and appropriate papillary muscle.

Figure 6A:
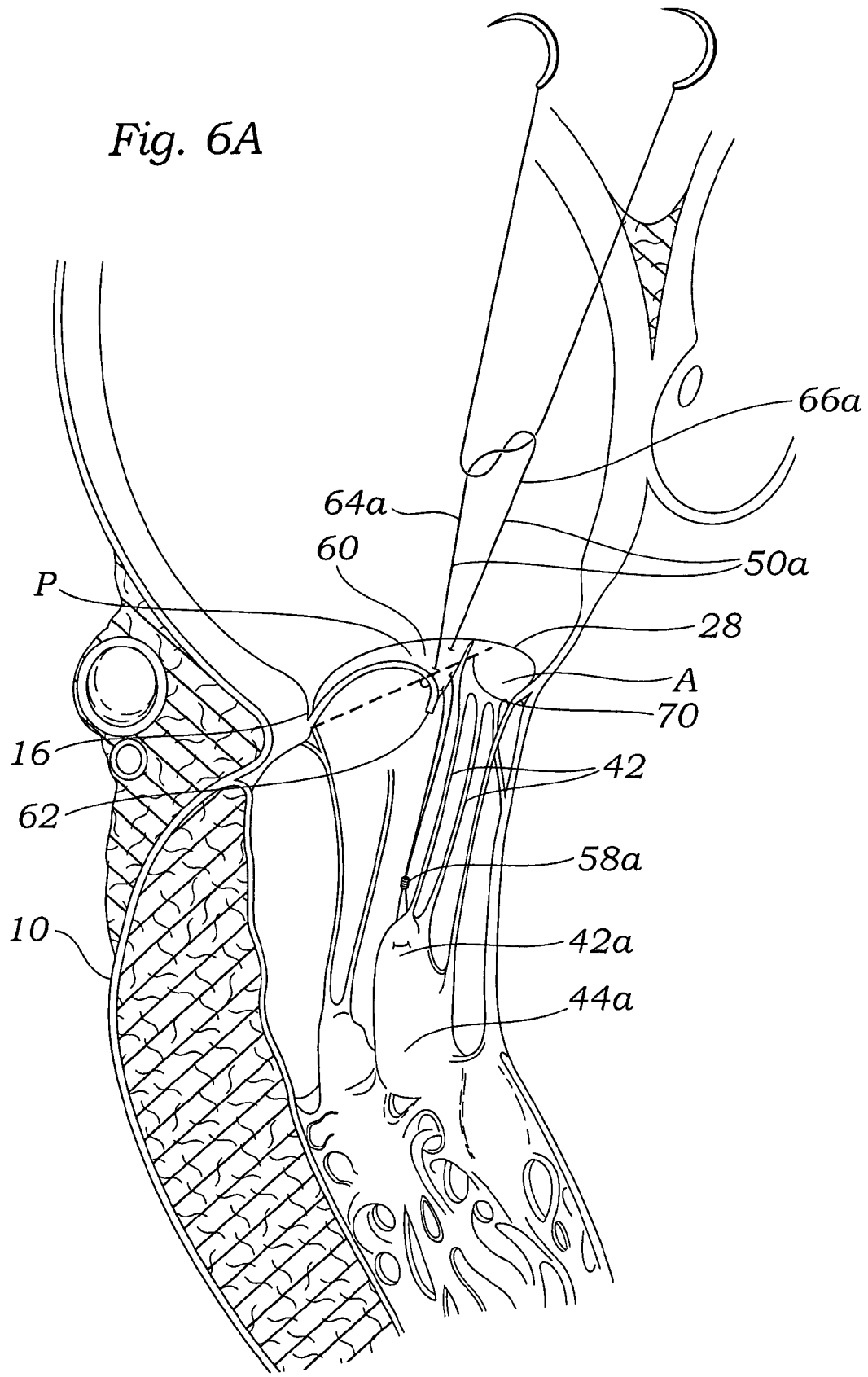
FIG. 6A is a side view of a mitral valve and papillary muscle with placement and tying of artificial chordae suture where there is no significant excess of tissue.
Figure 6B:
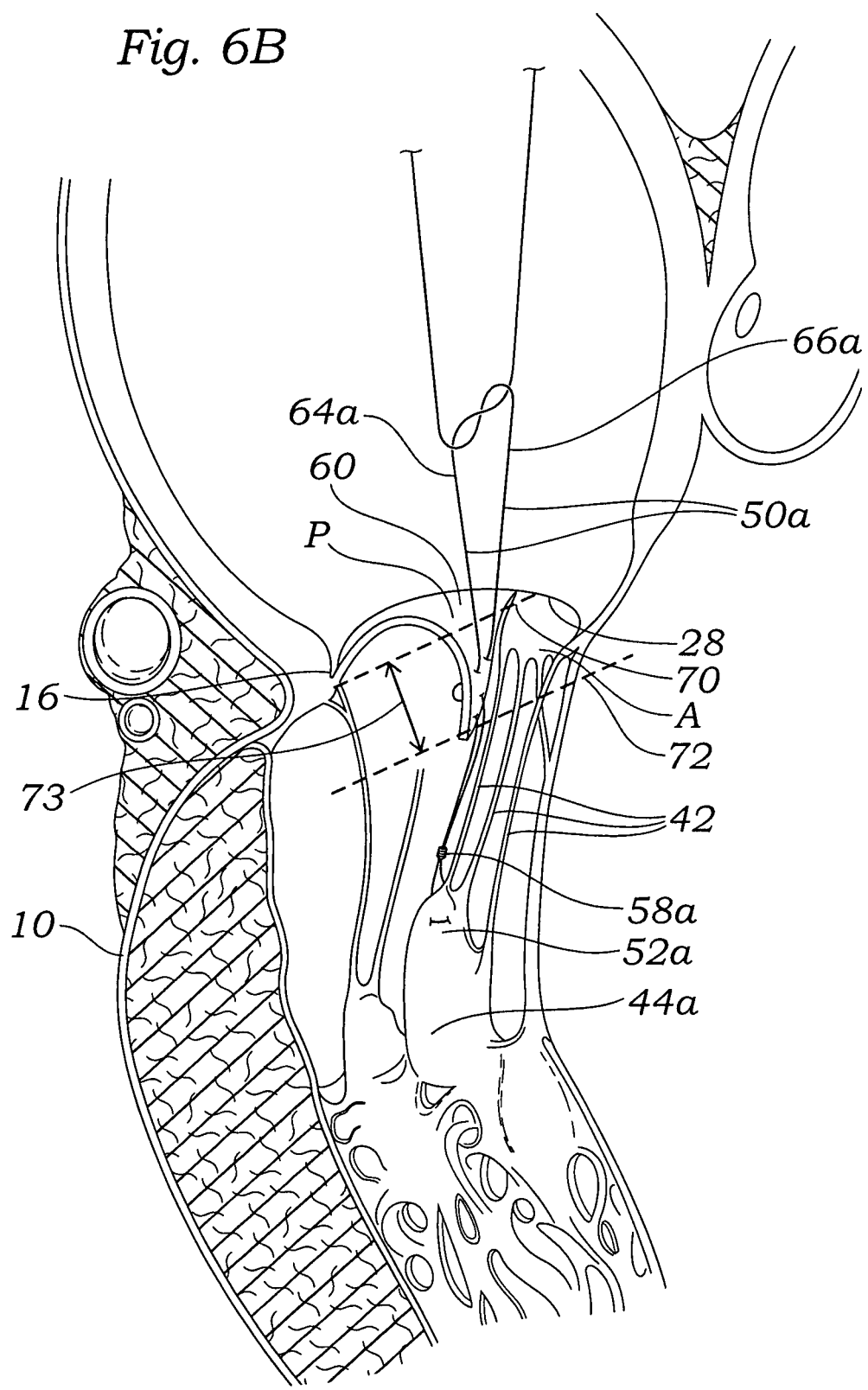
FIG. 6B is a side view of a mitral valve and papillary muscle with placement and tying of artificial chordae suture where there is an excess of tissue.

To ensure proper valve operation, the artificial chordae formed by the chordae replacement sutures 50a, 50p are tied off at a proper length. In the embodiment of FIGS. 6A and 6B, the stay sutures of the posterior leaflet P have been removed, so that the leaflet free edge 62 is freely mobilized.

Adjusting the length of the artificial chordae to the proper length should include consideration of the any excess leaflet tissue, which has been identified as a risk factor for postoperative SAM. Anterior displacement of the surface of coaptation towards the ventricular outflow tract has also been identified as a risk factor for SAM. To reduce the risk of SAM, the degree of correction of the prolapse of the posterior leaflet P should be such that the surface of coaptation remains vertical and posterior, parallel to the posterior wall of the left ventricle and away from the left ventricular outflow tract. In other words, if the excess tissue is large then the artificial chordae should be made shorter.

Depending on the particular application, the goal may include not only correction of the prolapse, but also transformation of the posterior leaflet into a vertical buttress against which the anterior leaflet will come into apposition to create a proper seal and prevent valve leakage. To achieve this, it is important that the free edge of the posterior leaflet is prevented from moving anteriorly towards the outflow tract of the left ventricle.

The length of the artificial chordae is selected to compensate for any excess of tissue of the posterior leaflet P. If there is no excess of tissue, then the artificial chordae length is selected to bring the free edge 62 of the posterior leaflet P to the level of the plane 70 of the valve annulus 28, as shown in FIG. 6A. If there is excess tissue, then the artificial chordae length is selected to bring the free edge 62 of the posterior leaflet P to a lower level 72, as shown in FIG. 6B. The lower level 72 is typically at a depth 73 between 5 mm and 8 mm underneath the plane 70 of the valve annulus 28, depending on the particular application and factors such as the height of the posterior leaflet P. Once the posterior leaflet free edge 62 is brought to the desired level, the chordae replacement sutures 50a, 50p are gently tied using one or more knots 74 on the auricular side 60 of the posterior leaflet P. In one embodiment three to four knots may be necessary, although other numbers of knots may also be used depending on the particular application.

Note that there may be variations on the particular manner in which the chordae replacement sutures are placed in and/or secured to the leaflets, depending on the particular application. For example, in the embodiments depicted in FIGS. 5B to 6B, the chordae replacement suture 50a passes from the auricular side 60 of the posterior leaflet P at or adjacent the free edge, then passes back through the posterior leaflet P at a distance of about 3 mm from the free edge. The chordae replacement suture 50a is then depicted being tied using a standard square knotting method. These suturing positions and distances could be varied, however, depending on the particular application and characteristics such as the strength of the particular leaflet tissue. A key issue to address for suture placement and securing is that the chordae replacement suture(s) should hold.

Figure 7:
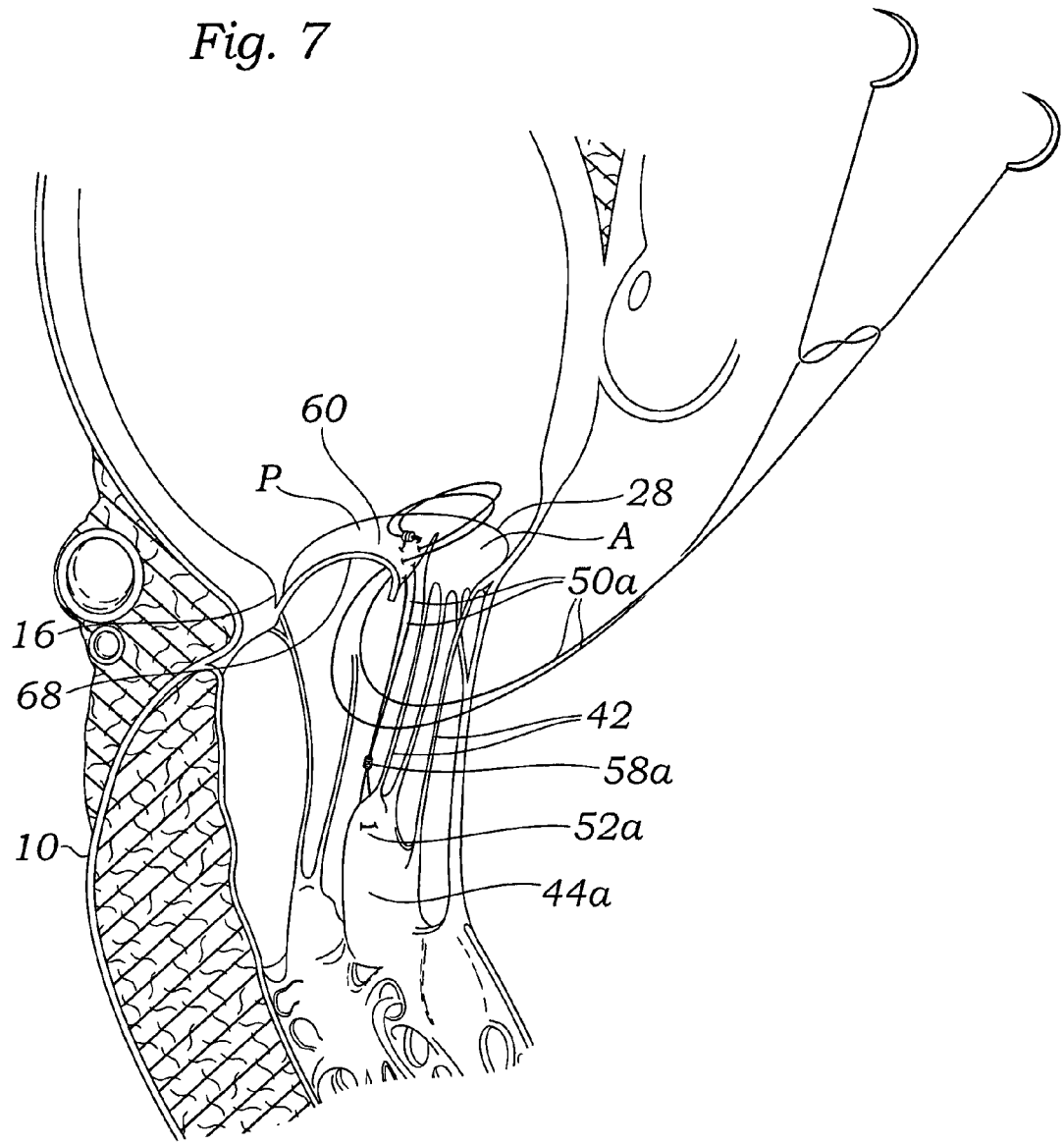
FIG. 7 is a side view of a mitral valve and papillary muscle with tying of the artificial chordae suture.

FIG. 7 depicts the chordae replacement suture 50a being passed again through the posterior leaflet P, and then tied on the ventricular side 68 of the posterior leaflet P. Depending on the particular application and the suture involved (e.g., if the chordae replacement suture(s) are a relatively slippery material, such as e-PTFE), a total of 10 to 12 knots may be necessary to tie off the chordae replacement suture, which can leave a relatively prominent remnant. Tying the final knot or knots on the ventricular side 68 can prevent excessive irregularity on the surface of coaptation due to any prominent remnant from the final knot, and also avoids any motion of the leaflet P along the chordae replacement suture which may create unnecessary repeated tension or other stress on the leaflet P and/or replacement chordae suture.

Figure 8:
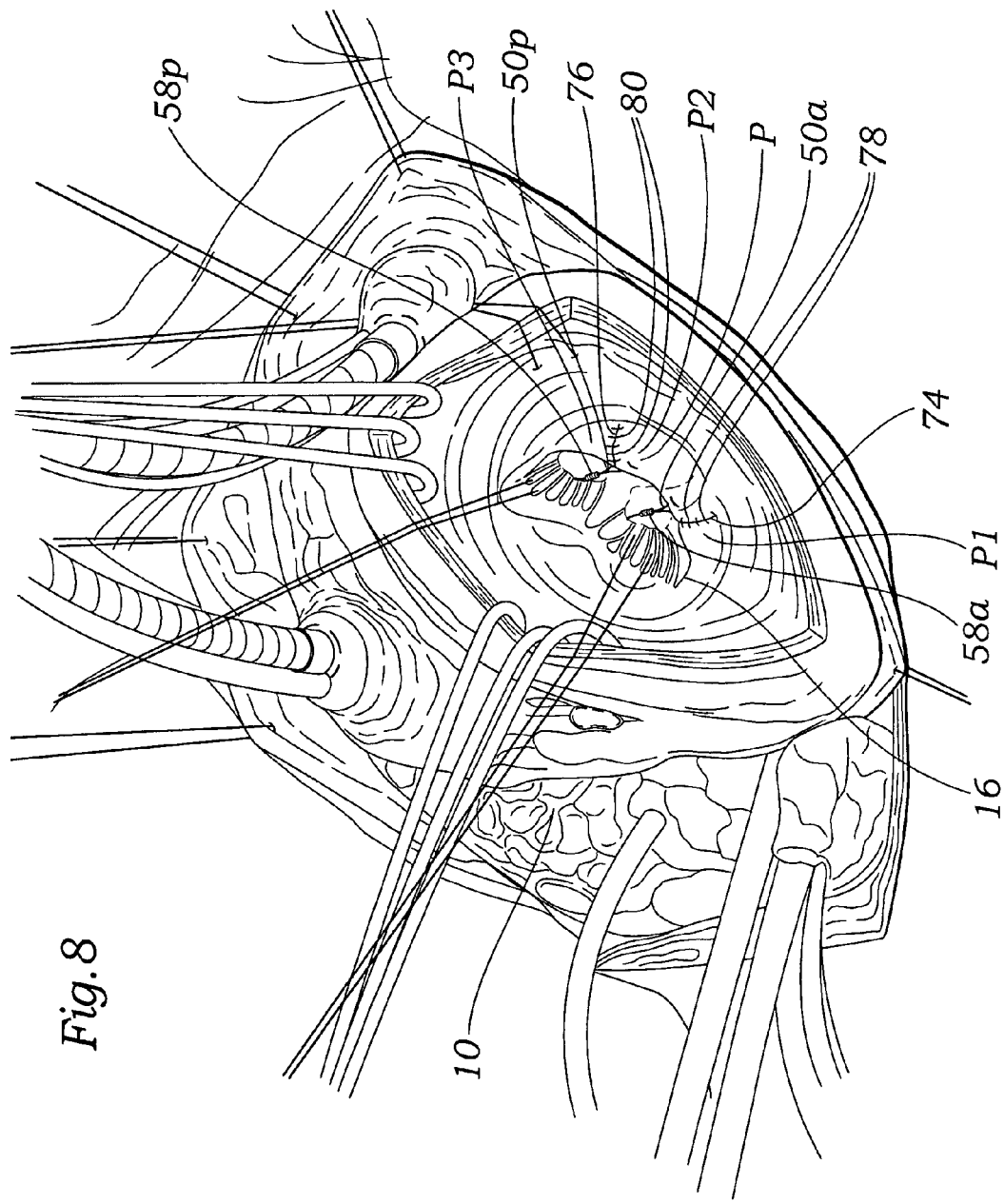
FIG. 8 is a top view of a mitral valve with sutures applied to the posterior leaflet indentations.

Most mitral valves have a naturally-occurring crease or indentation between P1 and P2, and another indentation between P2 and P3. If one or both of the indentations between P1 and P2 and between P2 and P3 are relatively deep, they may interfere with the goal of transforming the posterior leaflet into a relatively smooth and regular vertical buttress. In a natural and untreated mitral valve, these indentations serve the physiological purpose of making it possible for the posterior leaflet to expand slightly to follow the diastolic dilatation of the annulus without tension. However, if the annulus is to be fixed into the systolic position by the implantation of an annuloplasty ring, the indentations will no longer serve their useful role, and may instead interfere with proper valve function. For example, the indentations may be the cause of residual leak attributed by an irregular surface of coaptation. Accordingly, when the indentations are relatively deep and/or an annuloplasty ring is to be implanted, it may be desirable to suture the indentations. FIG. 8 depicts a mitral valve 16 with chordae replacement sutures 50a, 50p installed to create replacement chordae. The mitral valve 16 has an indentation 74 between P1 and P2, and another indentation 76 between P2 and P3. The indentations 74, 76 have been closed with suture 78, 80, such as a 5-0 monofilament running suture.

With the artificial chordae in place (and the indentations sutured, if desired), an annuloplasty ring may be installed. In the embodiment of such an installation in a mitral valve 16 depicted in FIG. 9, ring-securing sutures 82 (such as 2-0 breaded sutures) are passed through the mitral valve annulus 28 and then into the annuloplasty ring 84. The ring-securing sutures 82 are placed in a way that respects the desired geometry of the native valve 16. In the embodiment shown, four sutures 82 are placed at the level of the anterior leaflet A between the two commissures 86, and the remaining sutures 82 are placed adjacent the posterior leaflet P. The middle 30 of the anterior leaflet A corresponds to the middle 88 of the annuloplasty ring 84 to avoid any distortion of the mitral valve 16 from the desired geometry.

The role of the annuloplasty ring 16 is not only to reduce the size of the mitral valve annulus 28, but also to remodel the shape of the mitral valve 16, which is typically deformed as a consequence and/or cause of the mitral valve insufficiency. In fixing the mitral valve 16 in a systolic position, the annuloplasty ring 84 will prevent any further dilatation. The size of the annuloplasty ring 84 is selected according to various factors, such as the anterior leaflet surface area, the intertrigonal distance, etc.

After ring implantation, and before closure of the operational site, the result of the repair may be tested. In FIG. 9, the mitral valve 16 is tested by injecting saline 90 into the left ventricle using an injector 92. Two important goals are to confirm the absence of regurgitation and determine the aspect of the line of closure. The line of closure is typically preferred to be symmetrical, close to the ring, and parallel to the posterior aspect of the ring. A posterior line of closure indicates that the surface of coaptation is away from the ventricular outflow tract.

After closure of the left atrium and restoration of normal hemodynamic function, and echocardiographic analysis or other assessment of heart function can determine the quality of the result. The absence of regurgitation as well as a free (unobstructed) outflow tract signals a successful repair. Additionally, the height of the surface of coaptation can be measured, which is usually between 12 mm and 18 mm in a successful repair. For a successful treatment, the echocardiographic analysis typically will show a posterior leaflet with little or no mobility hanging vertically from the annulus and forming a buttress against which the anterior leaflet comes in apposition.

Referring again to FIGS. 6A and 6B, obtaining a desired length of the chordae replacement sutures 50a (50p not shown) is important in achieving a proper repair of the mitral valve 16. A guide that indicates the annular plane or other level at which to tie off the sutures could be helpful to a surgeon or other person installing the chordae replacement sutures. An embodiment of such a guide device 100 is depicted in FIGS. 10 and 11. The guide device 100 depicted includes a generally ring-shaped main body 102 which, in the embodiment depicted, is shaped similar to the annulus of the valve being treated. The guide device 100 is configured to be placed onto or into the mitral valve being treated. The guide device 100 includes one or more suture anchors 104, which are configured to receive suture to permit the guide device 100 to be temporarily sutured on or in the mitral valve annulus. The guide device 100 also includes a generally horizontal guide element in the form of a cross bar 106. In the particular embodiment depicted, the cross bar 106 is secured to the guide device 100 at a depth 107 of about 5 mm below the generally ring-shaped main body 102, although other cross bar depths are also within the scope of the invention. The selection of cross bar depth depends on the particular application, including such factors as the height of the leaflet to which the replacement chordae are to be attached, etc. Depths of between 0 and 8 mm are of specific interest to the invention.

The cross bar 106 is secured to the guide device 100 via a cross bar release mechanism which includes a first vertical bar 110 and a second vertical bar 112. The vertical bars 110, 112 each include a proximal portion 114, 116 that extends above the generally ring-shaped main body 102 of the guide device 100. Each of the vertical bars 110, 112 also includes a distal portion 118, 120 that is secured to the cross bar 106.

One vertical bar 110 is secured at its distal portion 118 to the cross bar 106 via a hinge in the form of a pin 122. The other vertical bar 112 includes a hole 124 configured to slidingly receive an end of the cross bar 106. Both of the vertical bars 110, 112 are secured to the generally ring-shaped main body 102 of the guide device 100 via at least partially flexible connections 126, 128. By pressing inwardly on the proximal portions 114, 116 of the vertical bars 110, 112 (i.e., by pressing the proximal portion of one vertical bar toward the proximal portion of the opposite vertical bar), the distal portions 118, 120 of the vertical bars 110, 112 are forced apart by the rotation of the vertical bars 110, 112 about the connections 126, 128. As the distal portions 118, 120 move apart, the cross bar 106 is pulled out of the hole 124, and is then free to rotate about pin 122 as depicted in FIG. 11.

Figure 12:
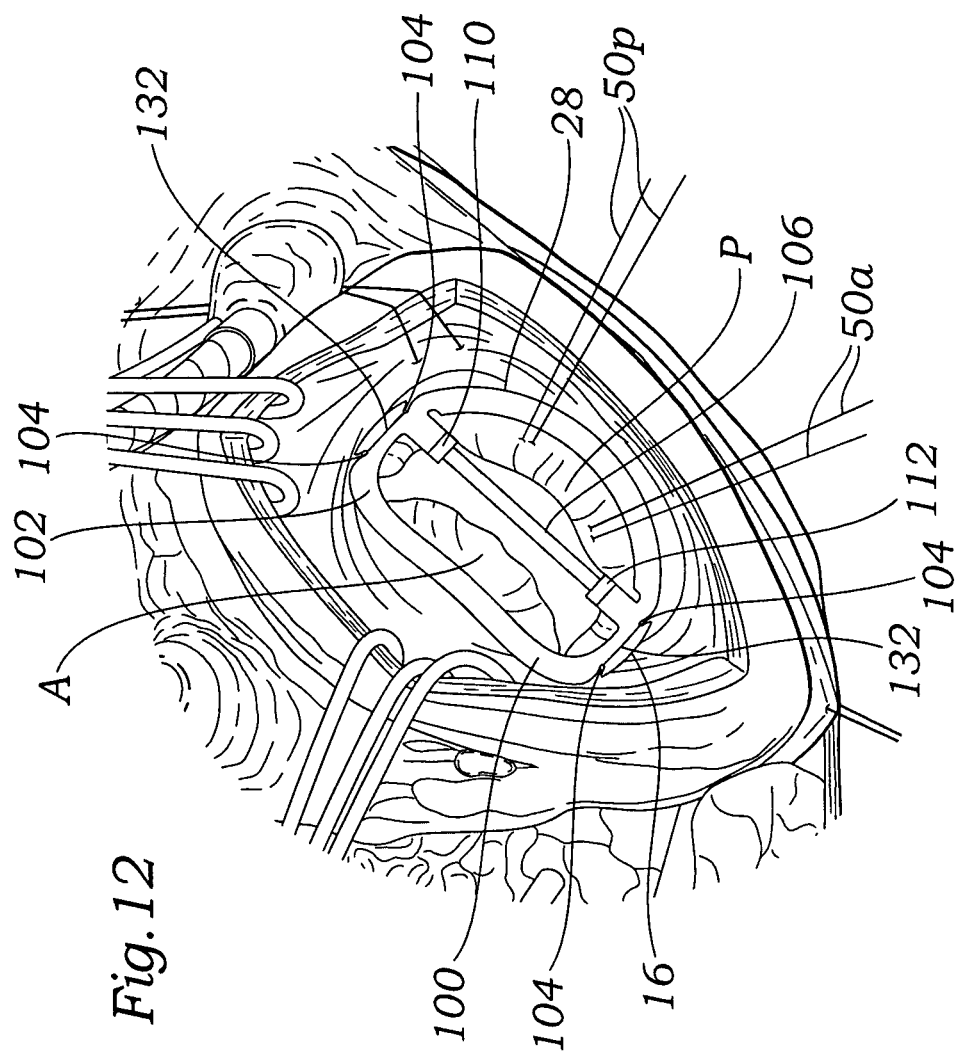
FIG. 12 is a top view of the guide device of FIGS. 10-11 positioned on or in a mitral valve annulus according to an embodiment of the invention.
Figure 13:
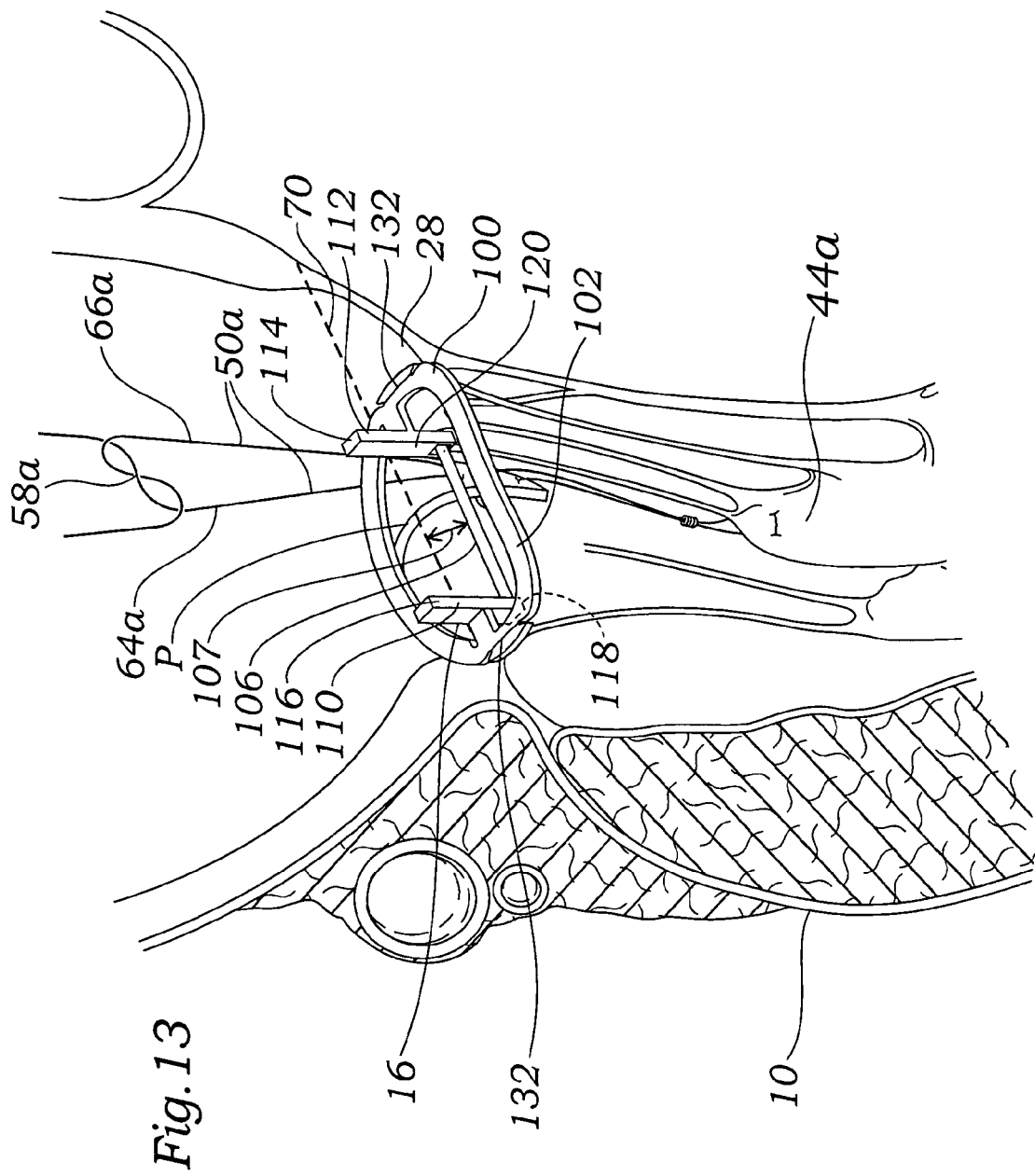
FIG. 13 is a side perspective view, in partial cross-section, of the guide device of FIGS. 10-11 positioned on or in a mitral valve annulus according to an embodiment of the invention.

In the embodiment of FIGS. 10 and 11, the "sub-valvular" assembly formed by the cross bar 106 and its supports (i.e., the vertical bar lower portions 118, 120) has a length 129 that is less than the maximum width 130 of the generally ring-shaped main body 102 of the guide device 100. The cross bar 106 is also held by the vertical bars 110, 112 at a position slightly inward from the periphery of the ring-shaped main body 102. The ring-shaped main body 102 is generally configured to match the shape of the annulus of the valve to be treated. As depicted in FIGS. 12-13, the "inward" positioning of the cross bar 106 and vertical element lower portions 118, 120 permits the cross bar 106 to be passed through the valve annulus 28 and between the valve leaflets A, P at a position that facilitates guiding the appropriate length at which to tie off replacement chordae sutures.

In the embodiment depicted in FIGS. 12 and 13, the guide device 100 is positioned on or in the valve annulus 28 prior to tying the chordae replacement suture(s) 50a, 50p to the valve posterior leaflet P. Depending on the particular application, the guide device 100 can be placed onto or into the valve annulus 28 after the chordae replacement suture(s) 50a, 50p have been secured to the respective papillary muscle(s) 44a (44p not shown), but prior to the chordae replacement suture(s) 50a, 50p being firmly tied to the valve posterior leaflet P. The guide device 100 is placed onto the valve annulus 28 with distal portions 118, 120 of the vertical bars 110, 112 extending through the valve annulus 28 and into the subvalvular area. This positions the cross bar 106 extending down into the valve annulus 28 into the ventricle area at a desired depth 107, which can be anywhere from 0 mm to 10 mm below the plane 70 of the valve annulus 28, depending on the particular application and such issues as the extent of excess posterior leaflet tissue, etc. In the particular embodiment depicted, the guide device 100 is positioned on or in the valve annulus 28 so that the ring-shaped main body 102 is generally parallel to the plane 70 of the valve annulus 28. For the particular guide device 100 depicted, which has a cross bar 106 generally parallel to the ring-shaped main body 102, the cross bar 106 will thus be positioned generally parallel to the plane 70 of the valve annulus 28.

With the guide device 100 in the desired position, the surgeon or other user can temporarily secure the guide device main body 102 to the valve annulus 28 using one or more stay sutures 132 passing through the suture anchors 104.

With the chordae replacement suture(s) tied to the papillary muscle(s), the surgeon or other user will proceed to tie the chordae replacement sutures to the valve leaflet, as previously depicted in FIGS. 5A to 7. As depicted in FIGS. 12 and 13, the cross bar 106 of the guide device 100 serves as an indicator of the proper height at which to tie the chordae replacement suture(s) 50a, 50p to the valve leaflet. As depicted in FIG. 13, the surgeon can pass the first arms 64a (64p not shown) and second arms 66a (66p not shown) of each replacement suture 50a (50p not shown) on either side of the cross bar 106, then tie one or more knots 58a (58p not shown) in the suture(s) so that the cross bar 106 is held between the suture knots 58a (58p not shown) and the posterior valve leaflet P. With the chordae replacement suture(s) 50a (50p not shown) thus secured to the posterior valve leaflet P at the desired length, the guide device 100 and cross bar 106 can be removed. In the device depicted in FIGS. 10-13, the user can squeeze together the proximal portions 114, 116 of the vertical bars 110, 112, thus releasing the cross bar 106 from one vertical bar 116 and permitting the cross bar 106 to be slid out from between the knots 58a (58p not shown) and the posterior valve leaflet P. The user can then tie additional finishing knots in the chordae replacement suture(s) 50a, 50p, as was previously depicted in FIGS. 7 and 8, to make the connection to the valve leaflet P more secure and/or permanent, and also to take in any slack in the chordae replacement sutures 50a, 50p that may have been created by the removal of the cross bar 106.

Figure 14A:
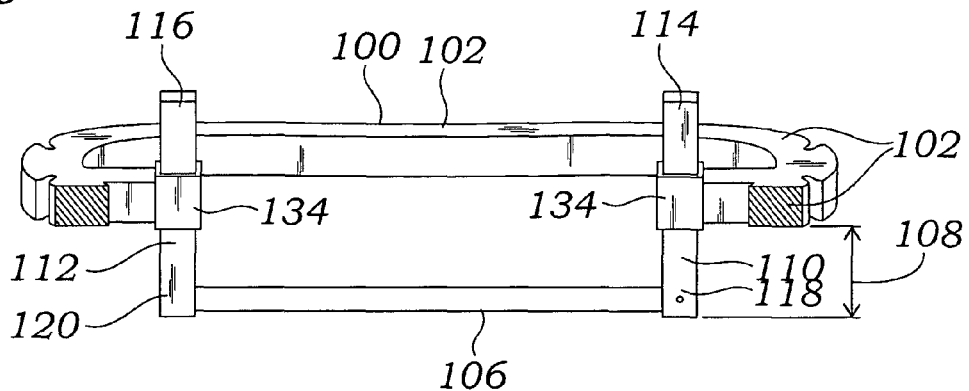
FIGS. 14A-14C are side views in partial cross section of a guide device according to an embodiment of the invention.
Figure 14B:
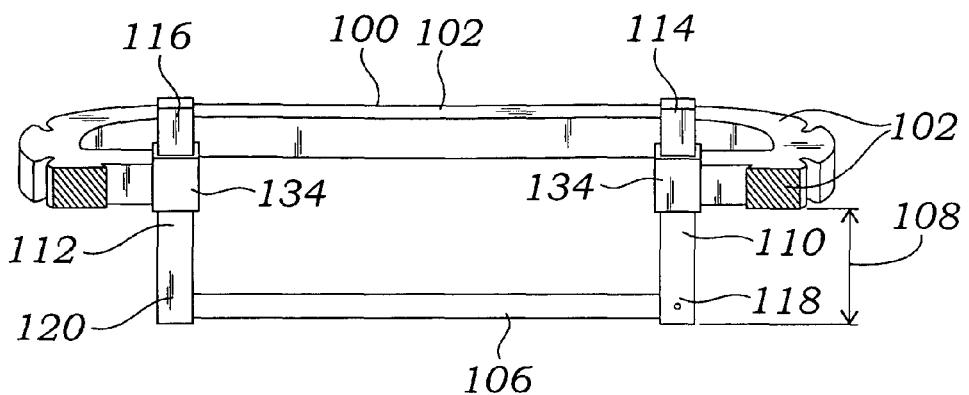
Figure 14C:
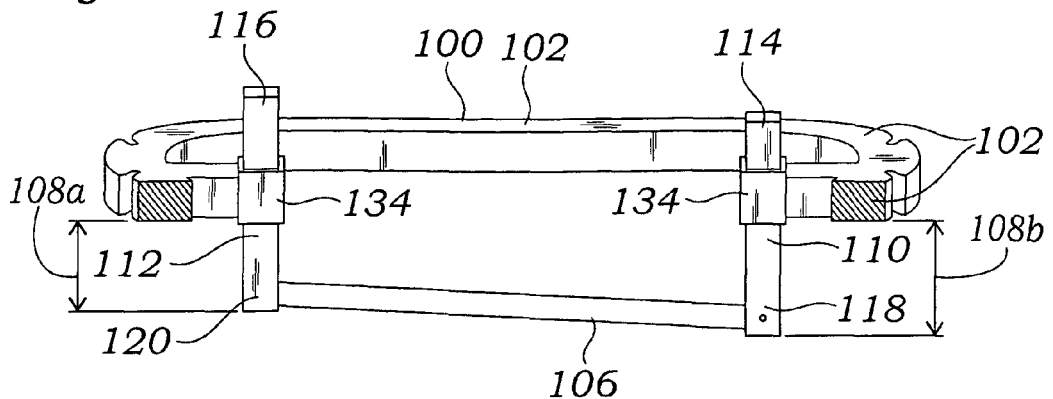

Depending on the particular application, the device could include a cross bar 106 having a depth 107 that is adjustable. For example, in the embodiment depicted in FIGS. 14A-14C, the vertical bars 110, 112 are secured to the main body 102 via connections 134 that permit the vertical bars 110, 112 to be raised and/or lowered with respect to the main body 102. One or more of the connections 134 may include a locking apparatus (not shown) for securing the vertical bars 110, 112 at the desired position once the vertical bars 110, 112 have been slid to that position(s). The locking mechanism could be one of many such devices and/or methods known in the art for locking a sliding element into position with respect to a fixed element. A user can thus select the desired depth at which to place the cross bar 106, slide one or both of the vertical bars 110, 112 up or down until the cross bar 106 is at the desired position, lock the connections 134 to secure the vertical bars 110, 112 and cross bar 106 in the desired position, and proceed to use the guide device 100 to determine the proper length for chordae replacement suture(s). In FIG. 14A, the cross bar depth 108 is relatively small, while in FIG. 14B the cross bar depth 108 is increased. In FIGS. 14A and 14B, the cross bar 106 is depicted as being generally parallel to the ring-shaped main body 102. However, by sliding the vertical bars 110, 112 to different depths 108a, 108b, as depicted in FIG. 14C, an angled configuration of the cross bar 106 can be achieved. Such an angled cross bar configuration could be selected for situations where different replacement chordae required different lengths. A device 100 such as that depicted in FIG. 14C thus has a cross bar 106 that is generally non-parallel from the ring-shaped main body 102. Placing the device 100 of FIG. 14C with the ring-shaped main body 102 on or in a valve annulus and also parallel to the plane of the valve annulus (in similar fashion to the position depicted in FIGS. 12 and 13 for the "parallel bar" device of FIGS. 10 and 11) would result in the cross bar 106 being in generally non-parallel relation to the plane of the valve annulus.

Figure 15:
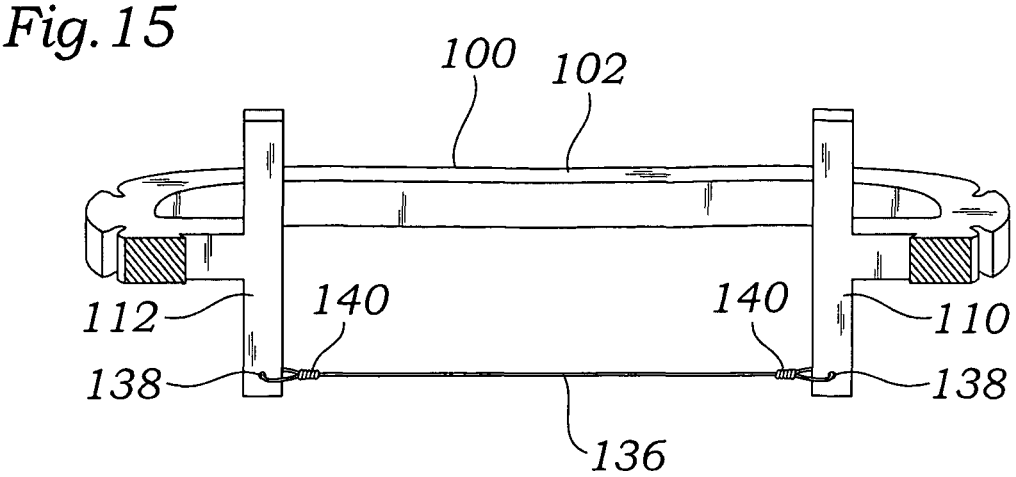
FIG. 15 is a side view in partial cross section of a guide device according to an embodiment of the invention.

The replacement chordae reference element, which in FIGS. 10-11 and FIGS. 14A-14C was a cross bar 106, could comprise a generally non-flexible member or a generally flexible member. In FIGS. 10-11 and 14A-14C, the cross bar 106 was a generally non-flexible bar. A flexible element, such as a flexible bar or flexible suture, could also be used. For example, in FIG. 15 a line of suture 136 is used as the cross bar reference element. The cross bar suture 136 is drawn relatively tightly between the vertical bars 110, 112, passing through to create a reference line positioned below and generally parallel with the guide device ring-shaped main body 102. in the particular embodiment depicted, the cross bar suture 136 is secured to the vertical bars 110, 112 by passing through suture holes 138 and then being tied in knots 140. In use, once the replacement chordae suture(s) have been tied off and it is desired to remove the guide device and cross bar suture, the cross bar suture can simply be cut with a scalpel by the surgeon or other user, and then the guide device removed and the remaining ends of the cross bar suture pulled from between the chordae replacement suture knots and the posterior leaflet.

Figure 16A:
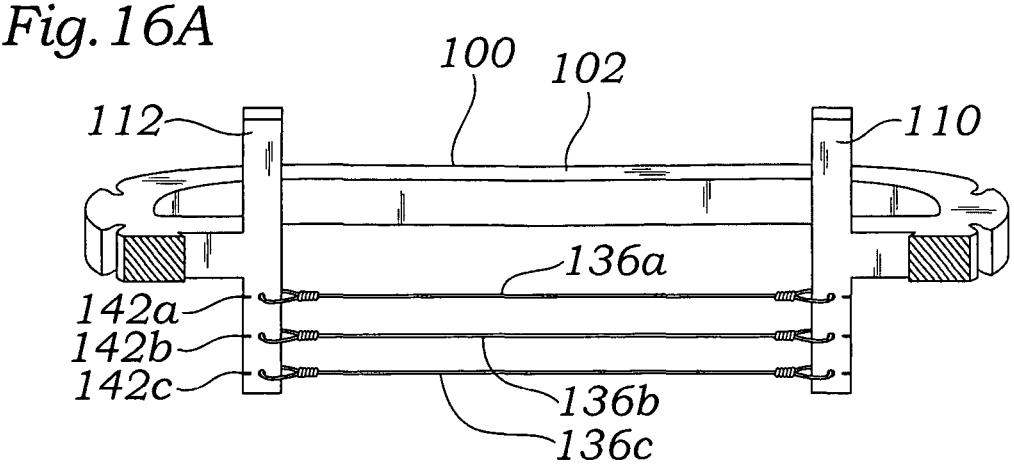
FIGS. 16A and 16B are side views in partial cross section of a guide device according to an embodiment of the invention.
Figure 16B:
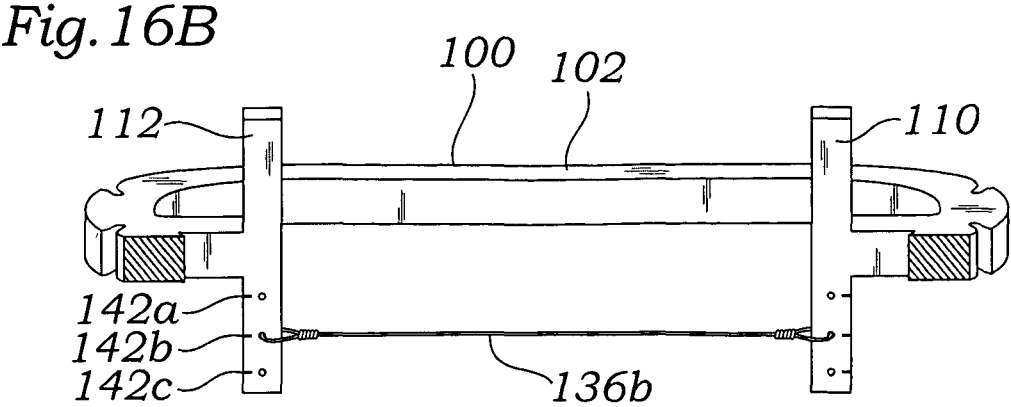

In another embodiment of the invention, multiple cross bars could be used, with the surgeon removing unwanted cross bars prior to employing the apparatus. For example, in the embodiment of FIGS. 16A and 16B, multiple lines of suture 136a, 136b, 136c are positioned at various depths on the vertical elements 110, 112. The guide device 100 includes depth markings 142a, 142b, 142c which indicate the depths of the respective suture bars 136a, 136b, 136c. The depth markings 142a, 142b, 142c depicted in FIGS. 16A and 16B are simple lines or notches, but other depth markings could alternatively or additionally be used, such as numbers, letters, or other markings, depending on the particular application. Prior to placing the guide device 100 on or into the valve annulus, the surgeon or other user can select the desired depth and remove those suture bars that are not at the desired depth, while retaining the suture bar that is at the desired depth. In FIG. 16B, the user has removed, via cutting or other means, the highest suture bar 136a and lowest suture bar 136c, thereby leaving middle suture bar 136b in place for use as the replacement chordae reference element. Note that the use of removable bar elements is not limited to suture bars, but could also use generally rigid bars, etc., configured to be selectively removed by a surgeon or other user.

Figure 17A:
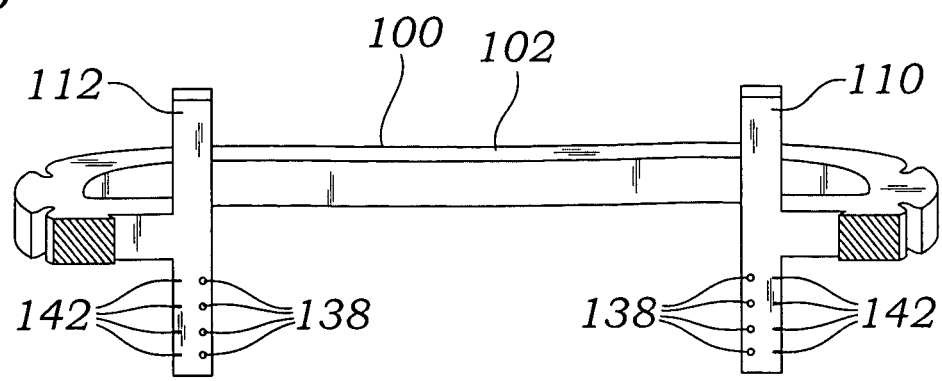
FIGS. 17A and 17B are side views in partial cross section of a guide device according to an embodiment of the invention.
Figure 17B:
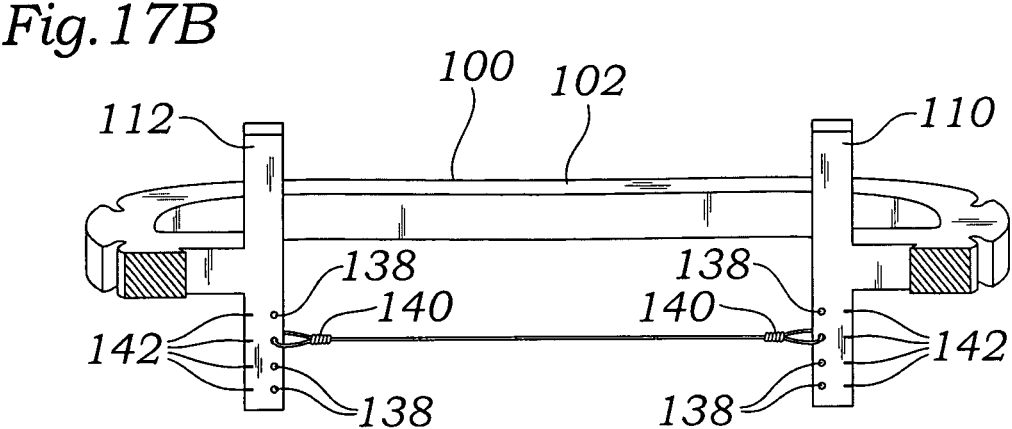

FIGS. 17A-17B depict a further embodiment of the invention, wherein the user selects the desired depth and installs the cross bar or other replacement chordae reference element at the desired depth. The device 100 of FIGS. 17A-17B includes two vertical bars 110, 112 each having several holes 138 or other suture-retaining elements along at least a part of the length of the vertical bars 110, 112. Depth markings 142 may also be included along the length of the vertical bars 110, 112 to indicate the "depth" of any cross bar suture that might be tied through a particular the hole (i.e., the distance of each hole from a plane passing through the guide device generally ring-like peripheral body and representing the plane of the valve annulus). A surgeon or other use can thus select the desired depth, determine which holes correspond to the desired depth, and then pass suture through a desired hole in one vertical bar to a desired hole in the second vertical bar. The surgeon or other user can thus tie off the suture line in knots 140 or via other retaining methods known in the art at a desired hole in each vertical bar 110, 112, thereby creating a device such as that depicted in FIG. 17B with a cross bar suture 136 extending between the vertical bars 110, 112 at the desired depth. The selected holes in each vertical element 110, 112, could be at the same level, as in FIG. 17B, thereby providing a cross bar suture 136 that is generally parallel to the ring-shaped main body 102. Alternatively, the selected holes from each vertical element could be at different levels, thereby providing a cross bar suture that is at angle from (i.e., non-parallel to) the ring-shaped main body 102. Such an embodiment would have similar characteristics, uses, and applications to that depicted in and discussed with respect to FIG. 14C.

In the embodiments discussed above, the discussion and figures have largely focused on replacing chordae for the posterior leaflet of the mitral valve. The invention could also be used, however, to replace other chordae, such as chordae of the mitral valve anterior leaflet or chordae of other valves.

Although the specific embodiment depicted and described involved an open surgical approach, the invention is also applicable to minimally invasive approaches, including percutaneous approaches (including accessing the treatment site through the circulatory system) and intercostal approaches (including accessing the treatment through the heart wall, including the apex of the heart).

While the invention can be performed without any valve leaflet resection, some resection may be desirable, depending on the condition of the heart valve leaflet. The invention can reduce the need and/or extent of any resection, but may need to be combined with some resection, particularly where a valve leaflet has a particularly large amount of excess tissue.

While the invention has been described with reference to particular embodiments, it will be understood that various changes and additional variations may be made and equivalents may be substituted for elements thereof without departing from the scope of the invention or the inventive concept thereof. For example, while the invention is specifically discussed in application with repair and/or replacement of chordae tendineae, it has applicability in other areas where it is desired to repair similar structures. In addition, many modifications may be made to adapt a particular situation or material to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. An apparatus for repairing a heart valve, comprising:
a generally ring-shaped main body having a shape and size similar to, and configured to be placed on or in, a heart valve annulus, the generally ring-shaped body defining an annular opening therethrough and a generally horizontal reference plane therethrough, the generally ring-shaped body having a maximum width;
first and second vertical members extending downwardly from, and generally perpendicularly to, the generally horizontal reference plane of the generally ring-shaped body, wherein the first and second vertical members are secured to the generally ring-shaped body at or adjacent opposing sides of the annular opening; and a generally horizontal reference element comprising a first end and a second end, wherein the generally horizontal reference element is generally parallel to the generally horizontal reference plane of the generally ring-shaped body, and wherein the generally horizontal reference element is positioned at a distance of 3 mm to 15 mm below the generally horizontal reference plane of the generally ring-shaped body, wherein the generally horizontal reference element has a length which is shorter than the maximum width of the generally ring-shaped main body, wherein the first end of the generally horizontal reference element is secured to the first vertical member, wherein the second end of the generally horizontal reference element is secured to the second vertical member, whereby the generally horizontal reference element defines a generally horizontal reference line extending in a straight line between the first vertical member and the second vertical member.

2. The apparatus of claim 1, wherein the first end of the generally horizontal reference element is secured to the first vertical member at a first distance from the support body reference plane, and the second end of the generally horizontal reference element is secured to the second vertical member at a second distance from the support body reference plane.

3. The apparatus of claim 2, wherein the first distance is substantially equal to the second distance.

4. The apparatus of claim 3, wherein the first distance is greater than the second distance.

5. The apparatus of claim 2, wherein the first reference element is configured to fit between adjacent valve leaflets of a heart valve when the support body is placed on or in a heart valve annulus of the heart valve.

6. The apparatus of claim 2, wherein the first reference element comprises a line of suture.

7. The apparatus of claim 2, wherein the apparatus is configured to provide variation in the first distance and in the second distance.

8. An apparatus for repairing a heart valve, comprising: a generally ring-shaped support body, the support body defining a periphery, an annular opening, and a generally horizontal support member reference plane therethrough, wherein the generally ring-shaped support body is configured for placement on or in a heart valve annulus; a first elongated member extending from the support body at a position adjacent a first end of the annular opening and in a direction away from and generally perpendicular to the support member reference plane, wherein the first elongated member has a proximal end positioned at or above the generally ring-shaped body, the first elongated member has a distal end positioned at least 3 mm below the generally ring-shaped body, and wherein the first elongate body proximal and distal ends are both positioned inward of the periphery of the generally ring-shaped support body when the generally ring-shaped body is viewed from above; and a second generally rigid elongated member extending from the support body at a position adjacent a second end of the annular opening and in a direction away from and generally perpendicular to the support member reference plane, wherein the second elongated member has a proximal end positioned at or above the generally ring-shaped body, the second elongated member has a distal end positioned at least 3 mm below the generally ring-shaped body, and wherein the second elongate body proximal and distal ends are both positioned inward of the periphery of the generally ring-shaped support body when the generally ring-shaped body is viewed from above, wherein the first end of the annular opening is an opposite end of the annular opening from the second end of the annular opening; and wherein the first elongated member comprises a plurality of first suture attachment points, the first suture attachment points positioned at different positions along the length of the first elongated member and below the generally ring-shaped support body; and wherein the second elongated member comprises a plurality of second suture attachment points, the second suture attachment points positioned at different positions along the length of the second elongated member and below the generally ring-shaped support body; and wherein a first suture line passing from one of the first suture attachment points to one of the second suture attachment points, wherein the first suture line is drawn relatively tightly between the one of the first suture attachment points and the one of the second suture attachment points and defines a generally straight line between the one of the first suture attachment points and the one of the second suture attachment points.

9. The apparatus of claim 8, further comprising:
indicia indicating the distance from one or more of the first suture attachment points to the support member reference plane.

10. The apparatus of claim 8, further comprising:
indicia indicating the distance from one or more of the second suture attachment points to the support member reference plane.

11. The apparatus of claim 8, wherein each of the first suture attachment points comprises a hole passing through the first elongated member.

* * * * *